United States Patent
Ogawa

(10) Patent No.: US 12,275,759 B2
(45) Date of Patent: Apr. 15, 2025

(54) HEPATITIS B VIRUS REPLICATION INHIBITOR AND PHARMACEUTICAL COMPOSITION FOR TREATING HEPATITIS B COMPRISING THE SAME

(71) Applicant: RIKEN, Saitama (JP)

(72) Inventor: Kenji Ogawa, Saitama (JP)

(73) Assignee: RIKEN, Saitama (JP)

( * ) Notice: Subject to any disclaimer, the term of this patent is extended or adjusted under 35 U.S.C. 154(b) by 865 days.

(21) Appl. No.: 17/284,142

(22) PCT Filed: Oct. 11, 2019

(86) PCT No.: PCT/JP2019/040154
§ 371 (c)(1),
(2) Date: Apr. 9, 2021

(87) PCT Pub. No.: WO2020/075836
PCT Pub. Date: Apr. 16, 2020

(65) Prior Publication Data
US 2021/0332089 A1    Oct. 28, 2021

(30) Foreign Application Priority Data
Oct. 12, 2018    (JP) .................................. 2018-193812

(51) Int. Cl.
| | |
|---|---|
| *C07K 14/02* | (2006.01) |
| *A61K 45/06* | (2006.01) |
| *A61P 31/20* | (2006.01) |
| *C07K 2/00* | (2006.01) |
| *A61K 38/00* | (2006.01) |

(52) U.S. Cl.
CPC .............. *C07K 14/02* (2013.01); *A61K 45/06* (2013.01); *A61P 31/20* (2018.01); *C07K 2/00* (2013.01); *A61K 38/00* (2013.01)

(58) Field of Classification Search
CPC ........... C07K 14/02; C07K 2/00; A61P 31/20; A61K 45/06; A61K 38/00
See application file for complete search history.

(56) References Cited

U.S. PATENT DOCUMENTS

2019/0183855 A1    6/2019    Ogawa

FOREIGN PATENT DOCUMENTS

| WO | WO2013/036973 | * | 3/2013 | |
| WO | WO-2013036973 A2 | * | 3/2013 | .......... A61K 31/713 |
| WO | 2018030534 A1 | | 2/2018 | |

OTHER PUBLICATIONS

McGonigle et al., An N-terminal extension to the hepatitis B virus core protein forms a poorly ordered trimeric spike in assembled virus-like particles, 2015, Journal of Structural Biology, 189: 73-80.*
Huang et al., Journal of Virology. 2012, vol. 86, No. 17, pp. 9443-9453 (Year: 2012).*
Wynne et al., Molecular Cell. 1999, vol. 3, pp. 771-780 (Year: 1999).*
Aspinall, EJ; et al., "Hepatitis B prevention, diagnosis, treatment and care: a review", Occup Med (Lond). 2011; vol. 61 (8); pp. 531-540.
Fattovich, G; et al., "Natural history of chronic hepatitis B: special emphasis on disease progression and prognostic factors"; J Hepatol. 2008; vol. 48(2); pp. 335-352.
Lau, DT; et al., "Long-term therapy of chronic hepatitis B with lamivudine", Hepatology 2000; vol. 32(4 Pt 1), pp. 828-834.
Koumbi, L, "Current and future antiviral drug therapies of hepatitis B chronic infection", World J Hepatol. 2015; vol. 7 (8), pp. 1030-1040.
Supplementary European Search Report for Corresponding European Application No. 19870375.3, 7 pages, Jul. 29, 1 2022.
Genbank accession No. AGS37006.1, Aug. 7, 2013, 1 page.
Genbank accession No. AGS79254.1, Nov. 4, 2013, 1 page.
Genbank accession No. ADM86020.1, Jul. 25, 2016, 1 page.

* cited by examiner

*Primary Examiner* — Lianko G Garyu
*Assistant Examiner* — Claudia Espinosa
(74) *Attorney, Agent, or Firm* — LUCAS & MERCANTI, LLP

(57) ABSTRACT

The purpose of the invention is to develop and provide a novel therapeutic agent for hepatitis B that differs from the conventional therapeutic agent for hepatitis B in the mechanism of action, or target of interest. Provided is an inhibitor of hepatitis B virus replication consisting of a spike region in the core protein of a hepatitis B virus, or an expression vector containing a nucleic acid encoding the same.

3 Claims, 14 Drawing Sheets

Specification includes a Sequence Listing.

Fig. 2
A
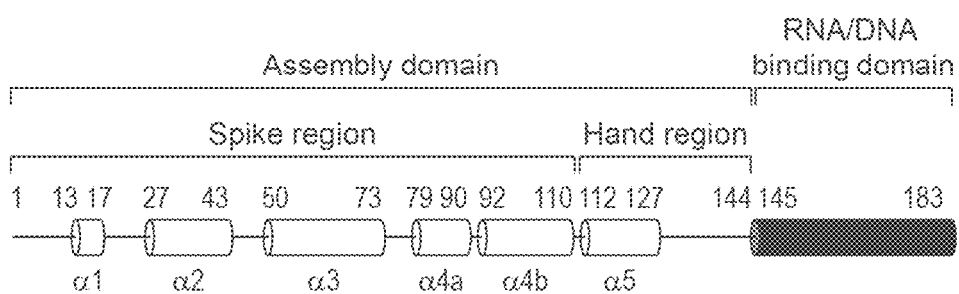
B
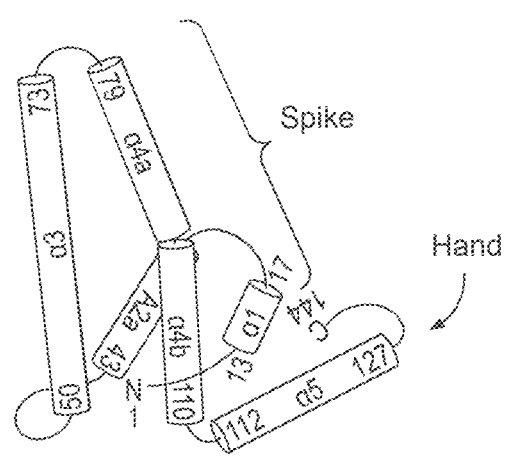
C
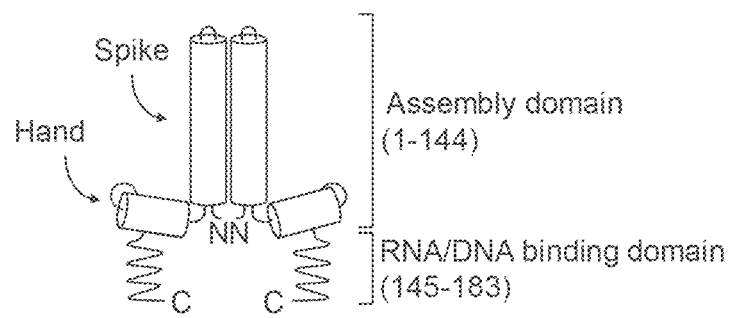

Fig. 3

```
                                α1                    α2
A     ------------MDIDPYKEFGATVELLSFLPSDFFPSVRDLLDTASALYREALESPEHC
B     ------------MDIDPYKEFGASVELLSFLPSDFFPSIRDLLDTASALYREALESPEHC
C     ------------MDIDPYKEFGASVELLSFLPSDFFPSIRDLLDTASALYREALESPEHC
D     ------------MDIDPYKEFGATVELLSFLPSDFFPSVRDLLDTASALYREALESPEHC
E     ------------MDIDPYKEFGATVELLSFLPSDFFPSVRDLLDTASALYRDALESPEHC
F     ------------MDIDPYKEFGASVELLSFLPSDFFPSVRDLLDTASALYRDALESPEHC
H     ------------MDIDPYKEFGASAELLSFLPSDFFPSVRDLLDTASALYREALESPEHC
G     MDRTTLPYGLFGLDIDPYKEFGATVELLSFLPSDFFPSVRDLLDTASALYRESLESSDHC
                  :************:***********:***********:***.:**

α3              α4a        α4b
A     SPHHTALRQAILCWGELMTLATWVGNNLEDPASRDLVVNYVNTMGLKIRQLLWFHISCL
B     SPHHTALRQAILCWGELMNLATWVGSNLEDPASRELVVSYVNVNMGLKIRQLLWFHISCL
C     SPHHTALRQAILCWGELMNLATWVGSNLEDPASRELVVSYVNVNMGLKIRQLLWFHISCL
D     SPHHTALRQAILCWGELMTLATWVGGNLEDPISRDLVVSYVNTNMGLKFRQLLWFHISCL
E     SPHHTALRQAILCWGELMTLATWVGVNLEDPASRDLVVSYVNTNMGLKFRQLLWFHISCL
F     TPNHTALRQAILCWGELMTLASWVGNNLEDPAARDLVVNYVNTHMGLKIRQLLWFHISCL
H     TPNHTALRQAILCWGELMTLASWVGNNLQDPAARDLVVNYVNTNMGLKIRQLLWFHISCL
G     SPHHTALRQAILCWGELMTLATWVGNNLEDPASRDLVVNYVNTNMGLKIRQLLWFHISCL
      :***************,**:*** **:** :*:***.***,:****:************

α5              RNA/DNA binding domain
A     TFGRETVLEYLVSFGVWIRTPPAYRPPNAPILSTLPETTVVRRRDRGRSPRRRTPSPRRR
B     TFGRETVLEYLVSFGVWIRTPPAYRPPNAPILSTLPETTVVRR---RGRSPRRRTPSPRRR
C     TFGRETVLEYLVSFGVWIRTPPAYRPPNAPILSTLPETTVVRR---RGRSPRRRTPSPRRR
D     TFGRETVIEYLVSFGVWIRTPPAYRPPNAPILSTLPETTVVRR---RGRSPRRRTPSPRRR
E     TFGRETVIEYLVSFGVWIRTPPAYRPPNAPILSTLPENTVVRR---RGRSPRRRTPSPRRR
F     TFGRETVLEYLVSFGVWIRTPPAYRPPNAPILSTLPETTVVRR---RGRSPRRRTPSPRRR
H     TFGRETVLEYLVSFGVWIRTPPAYRPPNAPILSTLPETTVVRQ---RGRAPRRRTPSPRRR
G     TFGRETVLEYLVSFGVWIRTPPAYRPPNAPILSTLPETTVVRR---RGRSPRRRTPSPRRR
      *******:*******************************,****:   ***:**********

A     RSQSPRRRRSQSRESQC (SEQ ID NO: 15)
B     RSQSPRRRRSQSRESQC (SEQ ID NO: 16)
C     RSQSPRRRRSQSRESQC (SEQ ID NO: 16)
D     RSQSPRRRRSQSRESQC (SEQ ID NO: 17)
E     RSQSPRRRRSQSPASQC (SEQ ID NO: 18)
F     RSQSPRRRRSQSPASQC (SEQ ID NO: 19)
H     RSQSPRRRRSQSPASQC (SEQ ID NO: 20)
G     RSQSPRRRRSASPASQC (SEQ ID NO: 21)
      ********* *  ***
```

Fig. 11
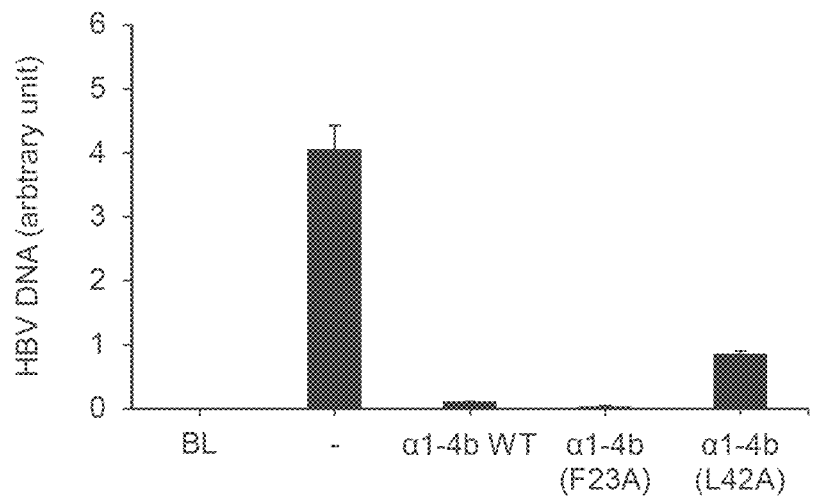
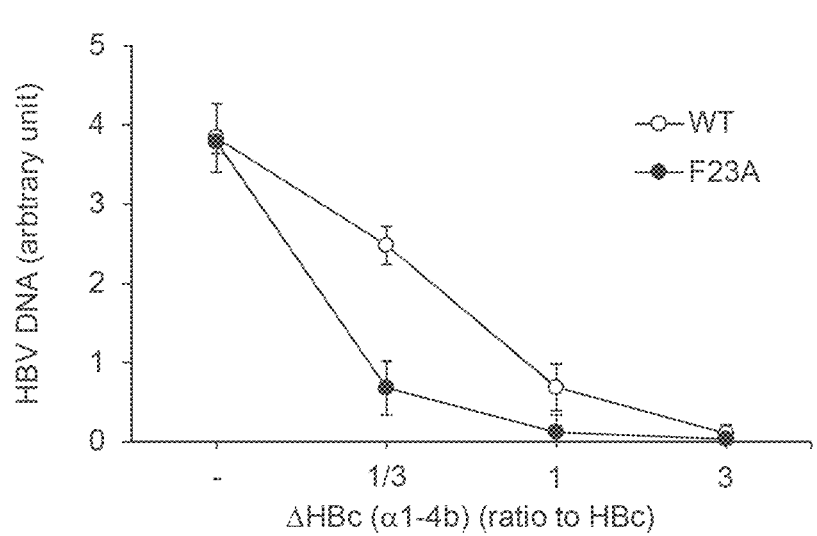

HEPATITIS B VIRUS REPLICATION INHIBITOR AND PHARMACEUTICAL COMPOSITION FOR TREATING HEPATITIS B COMPRISING THE SAME

CROSS-REFERENCE TO RELATED APPLICATIONS

This application is a 371 of PCT/JP2019/040154, filed Oct. 11, 2019, which claims the benefit of Japanese Patent Application No. 2018-193812, filed Oct. 12, 2018.

TECHNICAL FIELD

The present invention relates to an inhibitor of hepatitis B virus replication and a pharmaceutical composition for treating hepatitis B containing the same as an active ingredient.

BACKGROUND ART

Hepatitis B is viral hepatitis that is caused by infection with a hepatitis B virus (hepatitis B virus is herein often referred to as "HBV"). Since hepatitis B is transmitted through the blood or body fluid of an HBV infected person, vertical transmission in which a child is infected at the time of birth through the blood of the HBV infected mother (mother-to-child infection), and horizontal transmission caused by sexual contact, tattooing, blood transfusion, multiple use of a syringe in mass vaccination, a needle-stick accident, or the like are known as the main infection routes (Non-Patent Literature 1).

HBV infection can be largely classified into transient infection and persistent infection. Most infections at the age of 5 years or higher are transient infection, because their immunological competence has been well developed. Among them 70 to 80% are inapparent infections, and the remaining 20 to 30% develop acute hepatitis B. However, in most cases, an HBs antibody is induced, so that permanent immunity is acquired and development to persistent infection does not occur. On the other hand, persistent infection may be established in a case of mother-to-child infection, or a case where HBV infection occurs due to medical intervention or intrafamilial infection at the age of 3 years or lower when the immune system of the self is immature. The majority of patients with persistent infection of HBV go on to be "HBV carriers" who maintain normal hepatic function, of which 85 to 90% undergo seroconversion and become asymptomatic carriers. However, the remaining 10 to 15% develop chronic hepatitis which progresses to hepatic cirrhosis or hepatocellular carcinoma. The number of patients with persistent infection of HBV is estimated to be 1.5 million in Japan, and 300 to 400 million in the whole world (Non-Patent Literature 2).

Currently, nucleotide analog drugs represented by lamivudine or entecavir are widely used as therapeutic agents for chronic hepatitis B. These therapeutic drugs can delay the development and progression of hepatic cirrhosis and hepatocellular carcinoma by decreasing the amount of HBV in the blood through competitive antagonistic effects on the HBV DNA polymerase, or arresting effects on HBV DNA elongation. However, since the HBV DNA in hepatic cells cannot be eliminated, when the administration of a drug is stopped, the HBV DNA in the blood increases again and hepatitis relapse. Therefore, long-term administration of the therapeutic agent is necessary. In addition, relapse during the long-term therapy using the aforementioned nucleotide analog drug is accompanied by the emergence of a drug-resistant virus. This makes the treatment of chronic hepatitis B even more difficult (Non-Patent Literature 3 and 4). For the above reasons, it has been desired to develop a novel therapeutic agent for hepatitis B having a mechanism of action different from the conventional nucleotide analog drug.

CITATION LIST

Non Patent Literature

Non-Patent Literature 1: Aspinall E. J., et al., 2011, Occup Med (Lond), 61: 531-540.
Non-Patent Literature 2: Fattovich G., et al., 2008, J Hepatol, 48: 335-352.
Non-Patent Literature 3: Lau D. T., et al., 2000, Hepatology, 32: 828-834.
Non-Patent Literature 4: Koumbi L., 2015, World J Hepatol, 7: 1030-1040.

SUMMARY OF INVENTION

Technical Problem

An object of the present invention is to develop and provide a novel therapeutic agent for hepatitis B that differs from the conventional therapeutic agent for hepatitis B in the mechanism of action, or target of interest.

Solution to Problem

In order to solve the above problem, the present inventors attempted to develop a novel therapeutic agent for hepatitis B that inhibits the replication of HBV.

HBV is a DNA virus, and its genome consists of an approximately 3.2 Kb relaxed circular DNA (rcDNA) in which the positive strand ((+) strand) is shorter than the negative strand ((−) strand), and therefore there is partly a single-stranded structure as shown in FIG. 1. There are four kinds of genes, C, P, S, and X, on the HBV genome (Arzumanyan A, et al., 2013, Nat Rev Cancer., 13: 123-135). The ORF (open reading frame) of the C gene (C-ORF) is the main component of the nucleocapsid of HBV and encodes the core protein (HBc) and an HBe antigen, which are essential for replication of HBV. The ORF of the P gene (P-ORF) encodes the reverse transcriptase (HBV-Pol). Further, the ORF of the S gene (S-ORF) encodes three S protein regions (preS1, preS2, and S) which constitute the envelope, and the ORF of the X gene (X-ORF) is a transcriptional regulator and encodes the X protein (HBx), which is thought to be important in the establishment of hepatocellular carcinoma.

As for the mechanism of infection and replication of HBV, HBV first enters and infects a host hepatic cell via an unknown HBV-specific receptor. After the infection, the single-stranded portion is repaired in the host cell nucleus by an endogenous DNA polymerase derived from the host cell to form a covalently closed circular DNA (cccDNA). Next, using the (−) strand of the cccDNA as the template, four kinds of mRNAs with different lengths (3.5 kb, 2.4 kb, 2.1 kb, and 0.7 kb) are synthesized by the RNA polymerase II (RNA pol II) derived from the host cell. The longest 3.5 kb mRNA is called pregenomic RNA (pgRNA) and serves as the template for the HBV genomic DNA. The RNA encapsidation signal epsilon (ε) present at both the 5' and 3' ends of the pgRNA interacts with HBV-Pol and is incorporated into the nucleocapsid composed of HBc (Beck J, &

Nassal M., 2007, World J Gastroenterol., 13: 48-64). Subsequently, the negative strand DNA is synthesized by the reverse transcriptase activity using the pgRNA as the template. This process of genomic replication requires that the pgRNA is incorporated into the nucleocapsid together with HBV-Pol. The above mechanism of infection and replication of HBV suggests that the HBc is an extremely important protein which is the main component of the nucleocapsid constituting the main frame of a viral particle, and at the same time plays an essential role in genomic replication.

Therefore, the present inventors focused on HBc as the target protein of a novel therapeutic agent for hepatitis B that inhibits replication of HBV, and attempted to produce a mutant HBc that could antagonistically inhibit the replication of HBV.

Meanwhile, for verifying the above inhibitory effect on HBV replication, an experimental system that can accurately quantify and evaluate HBV replication is indispensable. Although there have ever been several evaluation systems for analyzing HBV infection or HBV replication, since infectious HBV is used, all of them are problematic in terms of safety and handling of a large amount of sample. In addition, the cells that can be efficiently infected with HBV are currently limited to a primary culture system of human hepatic cells, and expensive HepaRG® cells. Namely, there has been a strong limitation regarding applicable cells. Although infection can be established in cells where NTCP, which is considered to be an HBV receptor, is overexpressed, the efficiency of infection is very low, and even if an established cell line (HepG2.2.15, HepAD38, etc.) into which the HBV genome has been inserted is used, a long-term culture for 7 to 12 days is necessary before the detection of replication. Therefore, the conventional system for evaluating HBV replication had a serious problem of low throughput.

In order to solve the aforedescribed problems, the present inventors constructed in WO2018/030534 a system for evaluating HBV replication activity that can visualize the HBV genome replication in a short time, and quantify its activity inexpensively, safely, and rapidly using common cells without using infectious HBV. Further, the inventors succeeded in developing a novel HBV-Pol activity inhibitor using the system for evaluating HBV replication activity. This time, the inventors examined the effects of various deficient mutant HBcs on HBV replication using the HBV replication activity evaluation system described in WO2018/030534, and found mutant HBcs that acted antagonistically on HBc to significantly inhibit HBV replication. The present invention is based on the results of the research and provides the following.

(1) An inhibitor of HBV replication consisting of any of the following (I) to (III):
  (I) a peptide fragment constituting a spike region in a core protein of an HBV,
  (II) a peptide fragment in which any amino acid sequence different from said core protein is added to the N-terminus and/or C-terminus of said spike region, and
  (III) an expression vector comprising a nucleic acid encoding the peptide fragment according to said (I) or (II), and capable of expressing said peptide fragment in a cell.

(2) The inhibitor of HBV replication according to (1), wherein said peptide fragment constituting the spike region consists of any of the following amino acid sequences of (a) to (c):
  (a) the amino acid sequence according to any of SEQ ID NOs: 1 to 7,
  (b) an amino acid sequence in which one or multiple amino acids are added, deleted, or substituted in the amino acid sequence according to any of SEQ ID NOs: 1 to 7, and
  (c) an amino acid sequence having an amino acid identity of 82% or higher with the amino acid sequence according to any of SEQ ID NOs: 1 to 7.

(3) The inhibitor of HBV replication according to (1), wherein said nucleic acid consists of any of the following base sequences (i) to (iv):
  (i) the base sequence according to any of SEQ ID NOs: 8 to 14,
  (ii) a base sequence in which one or multiple bases are added, deleted, or substituted in the base sequence according to any of SEQ ID NOs: 8 to 14,
  (iii) a base sequence having a base identity of 80% or higher with the base sequence according to any of SEQ ID NOs: 8 to 14, and
  (iv) a base sequence that hybridizes under a high-stringent condition with a base sequence complementary to the base sequence according to any of SEQ ID NOs: 8 to 14.

(4) The inhibitor of HBV replication according to (2), wherein the phenylalanine (F) residue at position 23 is substituted with an alanine (A) residue and/or the leucine (L) residue at position 42 is substituted with an alanine (A) residue in the amino acid sequence according to any of SEQ ID NOs: 1 to 6, or the phenylalanine (F) residue at position 35 is substituted with an alanine (A) residue and/or the leucine (L) residue at position 54 is substituted with an alanine (A) residue in the amino acid sequence according to SEQ ID NO: 7.

(5) An inhibitor of nucleocapsid formation of a HBV, consisting of any of the following (I) to (III):
  (I) a peptide fragment constituting a spike region in a core protein of an HBV,
  (II) a peptide fragment in which any amino acid sequence different from said core protein is added to the N-terminus and/or C-terminus of said spike region, and
  (III) an expression vector comprising a nucleic acid encoding the peptide fragment according to said (I) or (II), and capable of expressing said peptide fragment in a cell.

(6) A pharmaceutical composition for treating hepatitis B comprising the inhibitor of HBV replication according to any one of (1) to (4) as an active ingredient, and a carrier and/or a solvent.

(7) The pharmaceutical composition for treating hepatitis B according to (6), further comprising an anti-HBV agent.

(8) The pharmaceutical composition for treating hepatitis B according to (7), wherein the anti-HBV agent is a nucleic acid analog and/or an HBV-Pol activity inhibitor.

(9) A method for inhibiting HBV replication comprising a step of introducing into a host:
  (I) a peptide fragment constituting a spike region in a core protein of an HBV,
  (II) a peptide fragment in which any amino acid sequence different from said core protein is added to the N-terminus and/or C-terminus of said spike region, or
  (III) an expression vector comprising a nucleic acid encoding the peptide fragment according to said (I) or (II), and capable of expressing said peptide fragment in a cell.

This application claims the priority based on Japanese Patent Application No. 2018-193812, the disclosure of which is incorporated herein by reference.

Advantageous Effects of Invention

The inhibitor of HBV replication of the present invention can be a novel anti-HBV agent.

With respect to the pharmaceutical composition for treating hepatitis B of the present invention, a pharmaceutical composition for treating hepatitis B having a mechanism of action or a target of interest different from the conventional therapeutic agent for hepatitis B can be provided by using an inhibitor of HBV replication of the present invention as an active ingredient.

BRIEF DESCRIPTION OF DRAWINGS

FIG. 2A is a schematic diagram of the domain structure of the HBV core protein (HBc). The HBc consists of 183 amino acids in full length, and is compose of an assembly domain (1 to 144 residues) at the N-terminus, and a RNA/DNA binding domain (145 to 183 residues) at the C-terminus. The assembly domain comprises five α-helices (α1 to α3, α4a, α4b, and α5). FIG. 2B: a schematic diagram of the three-dimensional structure of HBc (modified from Wynne, et al., 1999). The amino acids 1-111 (111 residues) comprising α1 through α4b on the N-terminal side constitute the spike structure of the capsid, and the amino acids 112-144 (33 residues) comprising α5 on the C-terminal side constitute the hand region. FIG. 2C is a schematic diagram of a HBc dimer. HBc forms a stable dimer serving as a unit, 90 or 120 of which assemble to form a regular-dodecahedral nucleocapsid.

FIG. 3 is a diagram showing the alignments of amino acid sequences each of which constitutes an HBc genotype. The asterisk at the bottom of the sequences indicates that the amino acids at the corresponding position are identical in all genotypes, and the colon indicates that the amino acids at the corresponding position are similar in all genotypes. The period indicates that the amino acids at the corresponding position are lacking in identity and similarity in some genotypes. The hyphen indicates a gap. In the upper part of the sequences, the positions corresponding to the respective domains of HBc are shown.

FIG. 5A is a schematic diagram of pBB-intron, which is an example of a vector for evaluating HBV replication activity. FIG. 5B is a schematic diagram of pCI-HBV-Pol, which is an expression vector for the P gene encoding HBV-Pol. FIG. 5C is a schematic diagram of pCI-HBc, which is an expression vector for the C gene encoding HBc. FIG. 5D is a schematic diagram of pCI-HBx, which is an expression vector for the X gene encoding HBx.

FIG. 7A to 7C show the results of evaluation of the effects of 11 kinds of ΔHBc constructed in Examples on HBV replication carried out by the system for evaluating HBV replication activity. In the figure, BL (Blank) indicates a mock of only HeLa cells without an expression vector introduced. The — indicates a positive control without pCI-ΔHBc introduced.

FIG. 10A shows the results of Western blotting under nonreducing conditions. In the diagram, Mlt stands for the band position of a multimer, T for that of a multimer, D for that of a dimer, and M for that of a monomer. WT stands for a full-length wild-type HBc, F23A for a full-length HBc-F23A, and L42A for a full-length HBc-L42A. FIG. 10B shows the results of particle blotting. FIG. 10C shows the HBV replication activity when the HBc expression vector comprised in the system for evaluating HBV replication activity is replaced with an F23A or L42A mutated HBc expression vector.

FIG. 11 shows the inhibitory effect on HBV replication by ΔHBc(α1-4b) having introduced F23A or L42A mutation. FIG. 11A shows inhibition of HBV replication by ΔHBc (α1-4b) having introduced point mutations in the system for evaluating HBV replication activity. FIG. 11B shows the result of the dose-dependent inhibitory effect on HBV replication.

FIG. 12A is the results of analysis of the effect of expression of PA-tagged ΔHBc(α1-4b) or ΔHBc(α1-4b)-F23A on HBc dimer formation and multimer formation performed by Western blotting using an anti-HBc monoclonal antibody #511. In the figure, Mlt stands for the band position of a multimer, T for that of a multimer, D for that of a dimer, and M for that of a monomer. FIG. 12B is the results of the analysis of the effect of expression of ΔHBc (α1-4b) or ΔHBc(α1-4b)-F23A on HBc dimer formation and multimer formation performed by Western blotting using an anti-PA monoclonal antibody NZ-1. FIG. 12C is the results of the analysis by Western blotting using the NZ-1 antibody after expression of ΔHBc(α1-4b)-PA alone, or co-expression with full length HBc in Hela cells. FIG. 12D is the results of particle blotting.

DESCRIPTION OF EMBODIMENTS

Figure 1:
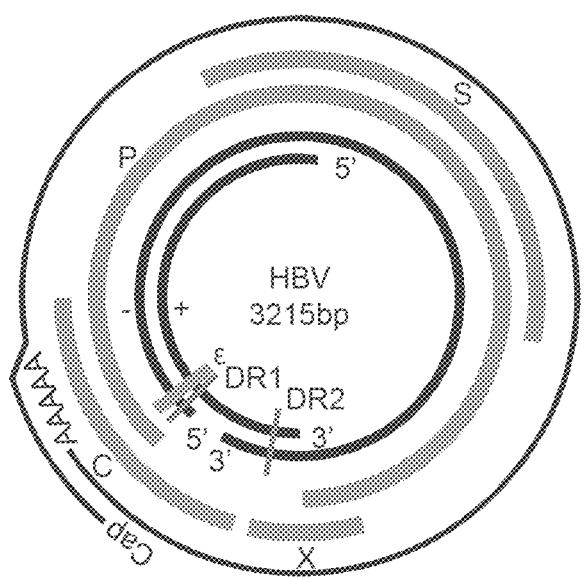
FIG. 1 is a schematic diagram of the genomic DNA structure of HBV. The central segment indicated by a black thick line is a relaxed circular genomic DNA (rcDNA) of HBV with a size of about 3.2 Kb. The gray thick lines are the ORF (open reading frames) of the four genes encoded in the genomic DNA of HBV, where C indicates the location of the C gene, P indicates that of the P gene, S indicates that of the S gene, and X indicates that of the X gene. The thin black line on the periphery indicates pregenomic RNA (herein often referred to as "pgRNA"), which is the longest mRNA having 3.5 kb among the mRNAs synthesized using the (−) strand of HBV genomic DNA as the template.

1. Inhibitor of Hepatitis B Virus Replication (Inhibitor of HBV Replication)

1-1. Outline

The first aspect of the present invention is an inhibitor of HBV replication. The inhibitor of HBV replication of the present invention consists of a peptide fragment constituting a spike region in a core protein (HBc), a peptide fragment in which any amino acid sequence different from said core protein is added to the N-terminus and/or C-terminus of the spike region, or an expression vector capable of expressing the spike region in a cell. The inhibitor of HBV replication of the present invention can be an active ingredient of a pharmaceutical composition for treating hepatitis B having a strong inhibitory effect on HBV proliferation in a hepatic cell.

1-2. Definitions

The terms used in the present specification are defined below.

"Hepatitis B virus (HBV)" is a DNA virus belonging to the family Hepadnaviridae, genus Orthohepadnavirus, and a causative virus of hepatitis B. As HBV, eight genotypes (genotype A, B, C, D, E, F, G, and H) are known based on differences in gene sequences. These genotypes differ in terms of regional distribution or pathological conditions. For example, in Japan patients infected with the genotype C (herein often referred to as "HBV/C". The same applies to other genotypes.) were conventionally dominant, and patients infected with HBV/B were in second place. However, patients infected with the HBV/A have been increasing recently. On the other hand, in Europe and the U.S., there are many patients infected with HBV/A and HBV/D. In the case of HBV/A, it is known that about 20 to 30% of patients after acute hepatitis contraction will develop chronic hepatitis, while in the case of HBV/B or HBV/C, the rate of development of chronic hepatitis after acute hepatitis contraction is lower.

The "core protein" (herein often referred to as "HBc") is a protein constituting nucleocapsid, which is essential for HBV replication. As shown in FIG. 2A, it is composed of an "assembly domain" on the N-terminal side, and, next to it, an "RNA/DNA binding domain" on the C-terminal side. The assembly domain is further composed of a "spike region" on the N-terminal side and, next to it, a "hand region (HR)" on the C-terminal side (Wynne S. A., et al., 1999, Mol Cell. 3: 771-780). HBc expressed in a virus-infected cell forms a dimer via the assembly domain (FIG. 2C), and a multimer consisting of 90 to 120 units in which the dimer is one unit is formed. The multimer constitutes a regular-dodecahedral HBV nucleocapsid. From crystal structure analysis and cryo-EM results, the assembly domain consists of five α-helices as shown in FIG. 2B, in which the spike region comprises four α-helices on the N-terminal side, and the hand region comprises one α-helix on the C-terminal side. As shown in FIG. 3, eight genotypes are known for HBc respectively corresponding to HBV/A to HBV/H. Herein each genotype of HBc is referred to as exemplified by the case of HBc of HBV/A referred to as "HBc/A". Each of HBc/A to HBc/F and HBc/H consists of 183 amino acid residues in full length, of which the assembly domain is composed of 144 amino acid residues from position 1 to 144, and the RNA/DNA binding domain is composed of 39 amino acid residues from position 145 to 183. Only HBc/G comprises an additional sequence consisting of 12 amino acid residues on the N-terminal side, and therefore its full length consists of 195 amino acid residues, in which the assembly domain is composed of 156 amino acid residues from position 1 to 156, and the RNA/DNA binding domain is composed of 39 amino acid residues from position 157 to 195. With respect to the full length amino acid sequence of each genotype of HBc, HBc/A is represented by SEQ ID NO: 15, HBc/B and HBc/C having completely identical amino acid sequences is represented by SEQ ID NO: 16, HBc/D by SEQ ID NO: 17, HBc/E by SEQ ID NO: 18, HBc/F by SEQ ID NO: 19, and HBc/H by SEQ ID NO: 20, while HBc/G having a full length different from other genotypes is represented by SEQ ID NO: 21.

The "C gene" is a gene encoding the core protein, and is one of the four genes encoded in the HBV genome, as described above.

An "expression vector" herein refers to a vector that comprises a gene or a gene fragment (hereinafter referred to as "gene or the like") in a state that allows for the expression thereof, and comprises an expression unit that can regulate the expression of the gene or the like. "A state that allows for the expression" herein means that a gene or the like to be expressed is located in the downstream region of a promoter under the control of the promoter. As a vector, a plasmid vector, a virus vector, and so on are known, and any of these vectors can be used. Normally, a plasmid vector, which can be readily manipulated by genetic recombination, may be used. A commercially available expression vector for mammalian cells may be used as the expression vector. Examples thereof include pCI vector, and pSI vector of Promega Corporation. The expression vector may also be a shuttle vector that can be replicated both in a mammalian cell and a bacterium such as *Escherichia coli*.

A "promoter" herein means a gene expression regulatory region that can regulate expression of a gene or the like located downstream (3' end side) in a cell having introduced an expression vector. A promoter can be classified into a ubiquitous promoter (systemic promoter) and a site-specific promoter, based on the location where the gene or the like under regulation of expression is expressed. A ubiquitous promoter is a promoter that regulates the expression of the gene or the like of interest in all cells, namely in the entire host individual. A site-specific promoter is a promoter that regulates the gene or the like of interest to be expressed only in a specific cell or tissue.

Further, a promoter is also classified into a constitutive active promoter, an expression inducible promoter, and a stage-specific active promoter, based on the timing of expression. A constitutive active promoter can constitutively express the gene or the like of interest in a cell. An expression inducible promoter can induce expression of the gene or the like of interest in a cell at any time. A stage-specific active promoter can induce expression of the gene or the like of interest in a cell only in a specific developmental stage. All of the above promoters may be interpreted as an overexpression promoter, since they can overexpress the gene of interest in a host cell.

"Inhibition of HBV nucleocapsid formation" herein means inhibition of functional nucleocapsid formation by inhibiting HBc dimer formation, or multimer formation with the dimer as a unit, or by inhibiting normal incorporation of pgRNA into the HBc multimer.

An "anti-HBV agent" herein refers to a drug having an effect that suppresses or inhibits replication or proliferation of HBV. The anti-HBV agent includes nucleic acid analog drugs, which are publicly known as therapeutic agents for treating chronic hepatitis B such as lamivudine and entecavir, and also the inhibitor of HBV replication of the present invention.

"Treatment" means herein alleviation or elimination of symptoms associated with contraction of a disease, and/or prevention or suppression of progression of a disease, and cure of a disease. A "disease" means herein hepatitis B, unless otherwise noted.

1-3. Composition

The inhibitor of HBV replication of the present invention consists of a peptide fragment, or an expression vector. The respective configurations are specifically described below.
(1) Peptide Fragment The "peptide fragment" constituting the inhibitor of HBV replication of the present invention consists of a spike region of HBV, or a peptide fragment in which any amino acid sequence different from the HBc is added to the N-terminus and/or C-terminus of the spike region. As described above, the spike region is a component comprised in the assembly domain of HBc on the N-terminal side. The spike regions of HBc/A to HBc/F, and HBc/H correspond to the 111 amino acid residues from position 1 to position 111 of HBc, and the spike region of HBc/G corresponds to the 123 amino acid residues from position 1 to position 123 of HBc. The amino acids in the spike region of each genotype is highly conserved, and among HBc/A to HBc/F, and HBc/H, the amino acid similarity is 95% or higher, and the amino acid identity is 84% or higher.

Specific examples of the amino acid sequence of the peptide fragment constituting the inhibitor of HBV replication of the present invention include the following (a) the amino acid sequence according to any of SEQ ID NOs: 1 to 7, (b) an amino acid sequence in which one or multiple amino acids are added, deleted, or substituted in the amino acid sequence according to any of SEQ ID NOs: 1 to 7, and (c) an amino acid sequence having an amino acid identity of 82% or higher, 84% or higher, 86% or higher, 88% or higher, 90% or higher, 92% or higher, 94% or higher, 96% or higher, or 98% or higher with the amino acid sequence according to any of SEQ ID NOs: 1 to 7. In the above, SEQ ID NO: 1 represents the amino acid sequence of the spike region derived from HBc/A, SEQ ID NO: 2 represents that derived from HBc/B and HBc/C, SEQ ID NO: 3 represents that derived from HBc/D, SEQ ID NO: 4 represents that derived from HBc/E, SEQ ID NO: 5 represents that derived from HBc/F, SEQ ID NO: 6 represents that derived from HBc/H, and SEQ ID NO: 7 represents that derived from HBc/G.

Herein, "multiple" means, for example, 2 to 20, 2 to 15, 2 to 10, 2 to 7, 2 to 5, 2 to 4, or 2 to 3. The amino acid substitution may be conservative amino acid substitution or nonconservative amino acid residue. "Conservative amino acid substitution" is a substitution between amino acids that have similar properties such as electric charge, side chain, polarity, and aromaticity. Amino acids with similar properties may be classified into, for example, basic amino acids (arginine, lysine, and histidine), acidic amino acids (aspartic acid, and glutamic acid), polar non-charged amino acids (glycine, asparagine, glutamine, serine, threonine, cysteine, and tyrosine), non-polar amino acids (leucine, isoleucine, alanine, valine, proline, phenylalanine, tryptophan, and methionine), branched amino acids (leucine, valine, and isoleucine), aromatic amino acids (phenylalanine, tyrosine, tryptophan, and histidine), etc.

Examples of amino acid substitution in an amino acid sequence constituting a peptide fragment include, but not limited to, a point mutation. Specific examples thereof include a point mutation by which the phenylalanine (F) residue at position 23 is substituted with an alanine (A) residue (herein this point mutation is referred to as "F23A". The same applies below.) and/or the leucine (L) residue at position 42 is substituted with an alanine (A) residue (L42A) in the amino acid sequence of the spike region according to any of SEQ ID NOs: 1 to 6. In another example of a point mutation, the phenylalanine (F) residue at position 35 is substituted with an alanine (A) residue (F35A), and/or the leucine (L) residue at position 54 is substituted with an alanine (A) residue (L54A) in the amino acid sequence of the spike region according to SEQ ID NO: 7.

The "amino acid identity" herein means, when two amino acid sequences are aligned and gaps are introduced as necessary to achieve the highest amino acid identity between them, the ratio (%) of identical amino acid residues between the above two amino acid sequences with respect to the total amino acid residues of one amino acid sequence. The amino acid identity can be calculated using a protein search system based on BLAST or FASTA.

There is no particular restriction on any amino acid sequence different from HBc added to the N-terminus and/or C-terminus of the spike region. Examples thereof include a ubiquitinated sequence, a nuclear transport signal, and a tag sequence. The peptide fragment can comprise one or more amino acid sequences of the spike region at either or both of the N-terminus and the C-terminus. The number of amino acids to be added is not limited, and may be, for example, 20, 19, 18, 17, 16, 15, 14, 13, 12, 11, 10, 9, 8, 7, 6, 5, 4, 3, 2, or 1, respectively.

(2) Expression Vector

The "expression vector" constituting the inhibitor of HBV replication of the present invention is an expression vector that comprises a nucleic acid encoding the peptide fragment described above and a promoter, and is capable of expressing the spike region described above in a cell. The expression vector may comprise, if necessary, such components as a marker gene (selection marker), an enhancer, a terminator, a replication origin, and a poly-A signal, in addition to the aforementioned components of nucleic acid and promoter. Each component is described below.

(Nucleic Acid)

A "nucleic acid encoding the peptide fragment constituting the spike region of HBc" may be one comprising a nucleic acid encoding the spike region of any of the aforementioned genotypes. There is no limitation as to the base sequence of such nucleic acid. Examples thereof include the base sequences of the genes of the respective genotypes encoded on the genome. Specific examples include a base sequence of the nucleic acid encoding the spike region of HBc/A of Accession No. AY707087.1; a base sequence of the nucleic acid encoding the spike region of HBc/B of Accession No. GU357842.1; a base sequence of the nucleic acid encoding the spike region of HBc/C of Accession No. AB033556.1; a base sequence of the nucleic acid encoding the spike region of HBc/D of Accession No. GU357846.1; a base sequence of the nucleic acid encoding the spike region of HBc/E of Accession No. X75664.1; a base sequence of the nucleic acid encoding the spike region of HBc/F of Accession No. JN792913.1; a base sequence of the nucleic acid encoding the spike region of HBc/G of Accession No. AB625342.1; and a base sequence of the nucleic acid encoding the spike region of HBc/H of Accession No. AP007261.1. A base sequence, in which the codons of the genes on the genome described above are optimized for expression in human cells, is also applicable. Specific examples thereof include a base sequence of the nucleic acid encoding the spike region of HBc/A according to SEQ ID NO: 8; a base sequence of the nucleic acid encoding the spike region of HBc/B or HBc/C according to SEQ ID NO: 9; a base sequence of the nucleic acid encoding the spike region of HBc/D according to SEQ ID NO: 10; a base sequence of the nucleic acid encoding the spike region of HBc/E according to SEQ ID NO: 11; a base sequence of the nucleic acid encoding the spike region of HBc/F according to SEQ ID NO: 12; a base sequence of the nucleic acid encoding the spike region of HBc/H according to SEQ ID NO: 13; and a base sequence of the nucleic acid encoding the spike region of HBc/G according to SEQ ID NO: 14. Note that in SEQ ID NOs: 8 to 14, a stop codon (TGA) is added to each 3' end in order to express only the spike region. Additional examples include a base sequence in which one or more bases are added, deleted, or substituted in any of the above base sequences, a base sequence having a base identity of 80% or higher, 82% or higher, 85% or higher, 88% or higher, 90% or higher, 93% or higher, 95% or higher, 98% or higher, or 99% or higher with any of the above base sequences, and a base sequence that hybridizes under a high-stringent condition with a base sequence complementary to any of the above base sequences.

Examples of base substitution in a base sequence constituting the nucleic acid include, but not limited to, a degenerate mutation, genetic polymorphism such as SNIPs, a splicing mutation, and a point mutation. Specific examples of a point mutation include a point mutation, by which TTC from position 67 to 69 is substituted with GCC, and/or CTG from position 124 to 126 is substituted with GCC in any of the base sequences according to SEQ ID NOs: 8 to 13. An additional example is a point mutation, by which TTC from position 106 to 108 is substituted with GCC, and/or CTG from position 160 to 162 is substituted with GCC in the base sequence according to SEQ ID NO: 14.

The "base identity" herein means, when two base sequences are aligned and gaps are introduced as necessary to achieve the highest base identity between them, the ratio (%) of identical bases between the above two base sequences with respect to the total bases of the base sequence according to either SEQ ID Number.

To "hybridize under a high-stringent condition" means herein that hybridization and wash are performed under a condition of low salt concentration and/or high temperature. For example, incubation is performed with a probe at 65° C. to 68° C. in 6×SSC, 5×Denhardt reagent, 0.5% SDS, and 100 µg/mL denatured fragmented salmon sperm DNA, and then washing is performed starting from room temperature in a 2×SSC, 0.1% SDS wash solution, and decreasing the salt concentration in the wash solution to 0.1×SSC and raising the temperature to 68° C. until no background signal is detected. For high-stringent hybridization conditions, Green, M. R., and Sambrook, J., 2012, Molecular Cloning: A Laboratory Manual Fourth Ed., Cold Spring Harbor Laboratory Press, Cold Spring Harbor, New York may be referred.

(Promoter)

A "promoter" is herein a promoter that can induce expression of the nucleic acid encoding the aforedescribed peptide fragment in a cell. Since the target cell to which the inhibitor of HBV replication of the present invention is applied, namely the expression vector is introduced, is in principle a mammalian cell, especially a human or chimpanzee-derived cell, any promoter that can express a downstream gene in those cells may be used. Examples thereof include a CMV promoter (CMV-IE promoter), a SV40 early promoter, a RSV promoter, an EF1α promoter, and a Ub promoter.

(Marker Gene)

A "marker gene" is herein a gene that encodes a marker protein, also called selection marker or reporter protein. A "marker protein" refers to a peptide whose activity can be used to determine the presence or absence of expression of a marker gene. For detecting the activity, the activity of the marker protein itself may be directly detected, or may be indirectly detected through a metabolite produced by the activity of the marker protein, such as a pigment. Detection may be performed by any of biological detection (including detection by binding of a peptide or a nucleic acid, such as antibody or aptamer), chemical detection (including detection by an enzymatic reaction), physical detection (including detection by behavioral analysis), or sensory detection by an inspector (including detection by vision, touch, olfaction, audition, or gustation).

There is no particular restriction on the type of a marker protein encoded by a marker gene, insofar as its activity can be detected by a method publicly known in the art. A marker protein which is less invasive to a transformant for the detection is preferable. Examples thereof include a tag peptide, a drug-resistant protein, a pigment protein, a fluorescent protein, and a luminescent protein.

A "tag peptide" is a short peptide consisting of a dozen to dozens of amino acids capable of labeling a protein, and is used for detecting or purifying a protein. Usually, a base sequence encoding a tag peptide is linked to the 5' end or the 3' end of the gene encoding the protein to be labeled, so as to express a fusion protein with the tag peptide, thereby labeling the protein. Various types of tag peptides have been developed in the field, and any tag peptide may be used. Specific examples of a tag peptide include FLAG, HA, His, and myc.

A "drug-resistant protein" is a protein that confers the resistance to a drug, such as an antibiotic added to a culture medium or the like, to a cell, and is often an enzyme. Examples thereof include β-lactamase conferring the resistance to ampicillin, aminoglycoside 3'-phosphotransferase conferring the resistance to kanamycin, tetracycline efflux transporter conferring the resistance to tetracycline, and CAT (chloramphenicol acetyltransferase) conferring the resistance to chloramphenicol.

A "pigment protein" is a protein involved in the biosynthesis of a pigment, or a protein that enables chemical detection of a transformant by a pigment through addition of a substrate, and is usually an enzyme. Here, a "pigment" is a low-molecular-weight compound or a peptide that can provide a pigment to a transformant, regardless of its type. Examples thereof include β-galactosidase (LacZ), β-glucuronidase (GUS), a melanin pigment synthesizing protein, an ommochrome pigment, and a pteridine pigment.

A "fluorescent protein" refers to a protein that emits fluorescence of a particular wavelength when irradiated with excitation light of a particular wavelength. It can be either of a natural type or a non-natural type. The excitation wavelength and the fluorescence wavelength are also not particularly limited. Specific examples thereof include CFP, RFP, DsRed (including derivatives such as 3×P3-DsRed), YFP, PE, PerCP, APC, and GFP (including derivatives such as EGFP and 3×P3-EGFP).

A "luminescent protein" refers to a substrate protein that can emit light without the need for excitation light, or an enzyme that catalyzes the light emission of the substrate protein. Examples thereof include luciferin and aequorin as the substrate protein, and luciferase as the enzyme.
(Enhancer)

Herein there is no particular restriction on an "enhancer", insofar as it can enhance the expression efficiency of a gene or a fragment thereof in a vector.
(Terminator)

A "terminator" herein means a sequence that can terminate the transcription of a gene or the like that is expressed by the activity of the aforedescribed promoter. The type of a terminator is not particularly limited. Preferably, it is a terminator derived from the same species as the promoter. A terminator that is paired with the aforedescribed promoter on the genome in a one-gene expression regulation system is particularly preferable.
(Replication Origin)

It is sufficient if the expression vector according to the present invention is able to transiently express the spike region of HBc in a mammalian cell. Therefore, the replication origin for a mammalian cell is not necessary. However, when it is a shuttle vector which requires expression in a bacterium, such as *E. coli*, a replication origin is indispensable. As the replication origin a publicly known sequence may be utilized. For example, fl origin can be used as the replication origin for *E. coli*.

1-4. Inhibitor of Formation of Hepatitis B Virus Nucleocapsid (Inhibitor of HBV Nucleocapsid Formation)

The target molecule for the inhibitor of HBV nucleocapsid formation is HBc. As described above, HBc is an essential protein for HBV genome replication, and at the same time the main component of a nucleocapsid, which constitutes the main frame of an HBV particle. In other words, the inhibitory effect on HBV nucleocapsid formation brings about at the same time an inhibitory effect on HBV replication. This effect is also demonstrated in Examples described herein. Therefore, the inhibitor of HBV replication of the present invention can also function as an inhibitor of HBV nucleocapsid formation. The configuration of the inhibitor of HBV nucleocapsid formation may be the same as that described in connection with the inhibitor of HBV replication.

2. Pharmaceutical Composition for Treating Hepatitis B

2-1. Outline

The second aspect of the present invention is a pharmaceutical composition for treating hepatitis B. The pharmaceutical composition for treating hepatitis B of the present invention comprises the inhibitor of HBV replication of the first aspect as an essential active ingredient, and can inhibit proliferation of HBV by inhibiting the replication of HBV after infection with HBV, thereby treating hepatitis B.

2-2. Configuration

2-2-1. Constituent

The constituents of the pharmaceutical composition for treating hepatitis B of the present invention are described below. The pharmaceutical composition for treating hepatitis B of the present invention comprises one or more active ingredients as essential constituents, as well as a solvent and/or a carrier, and further a drug delivery system (DDS) particle. Each constituent is described more specifically below.
(1) Active Ingredient The pharmaceutical composition for treating hepatitis B of the present invention comprises the inhibitor of HBV replication described in the first aspect as an essential active ingredient. It may also comprise one or multiple anti-hepatitis B virus agents (anti-HBV agents), as necessary.

Since the configuration of the inhibitor of HBV replication, which is the essential active ingredient, was described in detail in the first aspect, the explanation in detail is skipped here. The pharmaceutical composition for treating hepatitis B of the present invention may comprise one or multiple inhibitors of HBV replication.

The pharmaceutical composition for treating hepatitis B of the present invention may comprise only the essential inhibitor of HBV replication as the active ingredient, but it may also be a combination composition comprising additionally one or multiple other anti-HBV agents. Although there is no particular restriction on such other anti-HBV agents, examples thereof include publicly known anti-HBV agents such as a nucleic acid analog for treating hepatitis B, and an inhibitor of polymerase activity of hepatitis B virus (HBV-Pol activity inhibitor).

Examples of the "nucleic acid analog for treating hepatitis B" include Entecavir (ETV), Lamivudine (LAM), Adefovir, Tenofovir, Telbivudine, and Clevudine. All of them are pharmaceutical compositions for treating hepatitis B that inhibit the HBV reverse transcriptase activity.

The "HBV-Pol activity inhibitor" includes the phosphorylation inhibitor that inhibits phosphorylation of the activation site in HBV-Pol as described in WO2018/030534 developed by the present inventors. An example is a MAPK kinase inhibitor. More specific examples of the MAPK kinase inhibitor include Hypothemycin shown in the following Formula 1, Trametinib shown in Formula 2, PD98059 shown in Formula 3, PD184352 shown in Formula 4, and U-126 shown in Formula 5.

[Chem 1]

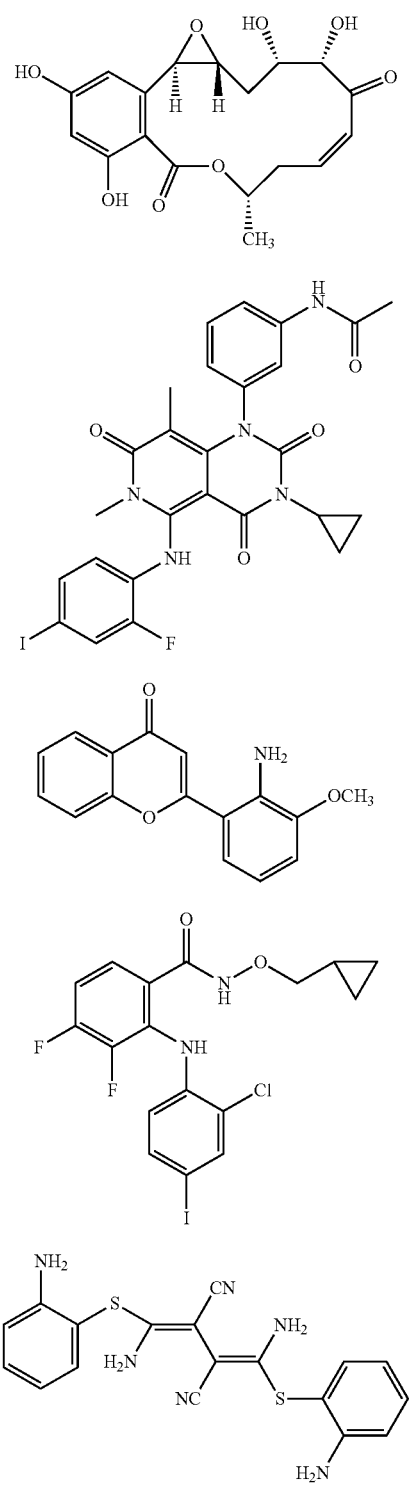

Since the nucleic acid analog for treating hepatitis B has a competitive antagonistic effect against an HBV DNA polymerase, and elongation arrest effect on HBV DNA, the mechanism of action is different from the inhibitor of HBV replication described in the first aspect which acts on HBV replication pathway. Further, the HBV-Pol activity inhibitor acts on HBV replication pathway similarly to the inhibitor of HBV replication. However, since the TxY motif is the target site, and a protein comprising the motif such as MAPK kinase is the target molecule, the target is different from the inhibitor of HBV replication described in the first aspect which uses HBc DNA as the target molecule. Consequently, when an inhibitor of HBV replication described in the first aspect is used in combination with another anti-HBV agent such as a nucleic acid analog for treating hepatitis B and/or an HBV-Pol activity inhibitor, a synergistic effect on anti-HBV inhibition can be obtained.

There is no particular restriction on the content of an active ingredient in the pharmaceutical composition for treating hepatitis B of the present invention. In general, the content should adjust depending on the type of an active ingredient, dosage form, and the type of a solvent or a carrier, which are other constituents described below. Therefore, it may be determined as appropriate by taking the respective conditions into consideration. A single dose of a pharmaceutical composition for treating hepatitis B should contain an effective amount of active ingredient. However, if it is necessary to administer a large amount of pharmaceutical composition for treating hepatitis B to a subject in order to obtain the pharmacological effect of the active ingredient, it may be divided into several doses so as to reduce the stress on subject. In this case, the effective amount of the active ingredient should be contained in the total doses. The "effective amount" refers to the amount necessary to function as the active ingredient, and at the same time the amount that causes little or no adverse side effects on the subject to be treated. This effective amount can adjust depending on a variety of conditions such as information about the subject, route of application, and number of application. Therefore, when a pharmaceutical composition for treating hepatitis B is used as a medicine, the amount of active ingredient is ultimately determined by the judgment of a physician, a pharmacist, etc.

A "subject" means herein an object to which an inhibitor of HBV replication described in the first aspect, or a pharmaceutical composition for treating hepatitis B of this aspect is applied. Examples thereof include a cell (including cultured cell), a tissue, an organ, and an individual. In the case of an individual, it is preferably a human individual, in which case it is specifically denoted as "subject person". A subject person infected with HBV, namely a patient with hepatitis B is particularly preferred.

The "information on a subject" herein refers to various information about the characteristics and conditions of a subject. For example, when the subject is a human individual, examples thereof include age, weight, gender, general health conditions, presence or absence of disease, stage of progression or severity of disease, drug sensitivity, presence or absence of concurrent medication, and tolerance to treatment.

(2) Solvent

The pharmaceutical composition for treating hepatitis B of the present invention may comprise a pharmaceutically acceptable solvent as needed. The term "pharmaceutically acceptable solvent" refers to a solvent normally used in the technical field of drug formulation. Examples thereof include water or an aqueous solution, and an organic solvent.

Examples of an aqueous solution include physiological saline, an isotonic solution containing glucose or another supplement, a phosphate buffer solution, and a sodium acetate buffer solution. Examples of an adjuvant include D-sorbitol, D-mannose, D-mannitol, sodium chloride, as well as a low-concentration nonionic surfactant, and a polyoxyethylene sorbitan fatty acid ester. Examples of an organic solvent include ethanol.

(3) Carrier

The pharmaceutical composition for treating hepatitis B of the present invention may comprise a pharmaceutically acceptable carrier as needed. The "pharmaceutically acceptable carrier" refers to an additive normally used in the technical field of drug formulation. Examples thereof include an excipient, a binder, a disintegrating agent, a filler, an emulsifier, a flow regulating additive, a lubricant, and a human serum albumin.

Examples of an excipient include a saccharide such as monosaccharide, disaccharide, cyclodextrin, and polysaccharide, a metal salt, citric acid, tartaric acid, glycine, polyethylene glycol, Pluronic, kaolin, silicic acid, and a combination thereof.

Examples of a binder include starch paste made from plant starch, pectin, xanthan gum, single syrup, a glucose solution, gelatin, tragacanth, methylcellulose, hydroxypropylmethylcellulose, sodium carboxymethylcellulose, shellac, paraffin, polyvinylpyrrolidone, and a combination thereof.

Examples of a disintegrating agent include the aforementioned starch, lactose, carboxymethyl starch, crosslinked polyvinylpyrrolidone, agar, laminaran powder, sodium hydrogen carbonate, calcium carbonate, alginic acid or sodium alginate, polyoxyethylene sorbitan fatty acid ester, sodium lauryl sulfate, stearic acid monoglyceride, and a salt thereof.

Examples of a bulking agent include vaseline, the aforementioned saccharide and/or calcium phosphate.

Examples of an emulsifier include a sorbitan fatty acid ester, a glycerol fatty acid ester, a sucrose fatty acid ester, and a propylene glycol fatty acid ester.

Examples of a flow regulating additive and a lubricant include a silicate, talc, a stearate, and polyethylene glycol.

In addition to the above, if necessary, a solubilizer, a suspending agent, a diluent, a dispersing agent, a surfactant, a soothing agent, a stabilizer, an absorption enhancer, a bulking agent, a moisturizer, a humectant, a wetting agent, an adsorbent, a corrective, a disintegration inhibitor, a coating agent, a colorant, a preservative, an antiseptic, an antioxidant, a fragrance, a flavoring agent, a sweetness agent, a buffer agent, an isotonizing agent, etc. which are used usually in a pharmaceutical composition, etc., may also be comprised as appropriate.

A carrier is used to avoid or inhibit degradation of the aforementioned active ingredient by an enzyme or the like in a subject, and also to facilitate formulation or administration method, as well as to maintain the dosage form and drug efficacy. It may be used as appropriate if it is necessary.

(4) Drug Delivery System Particle (DDS Particle)

The pharmaceutical composition for treating hepatitis B of the present invention can include a DDS particle as needed. The DDS particle is a particle that comprises an active ingredient, other carrier, etc., in the inside, etc., and delivers the content, especially the active ingredient without degrading the same to the target site, and can regulate the distribution of a drug in vivo in terms of time and quantity. Since the active ingredient in the pharmaceutical composition for treating hepatitis B of the present invention is a peptide or a nucleic acid, it is appropriate to use the DDS particle for protecting it from degradation by a protease or a nuclease in vivo after administration. Any type of DDS particle can be used. Examples thereof include a liposome, polymeric micelle, and a viral particle.

2-2-2. Dosage Form

There is no particular restriction on the dosage form of the pharmaceutical composition for treating hepatitis B of the present invention, insofar the dosage form allows delivery to the target site without inactivating the active ingredient in the body of the subject.

The specific dosage form varies depending on the application method described below. The application methods can be broadly classified into parenteral administration and oral administration, and the dosage form should be suitable for each administration method.

For example, in a case where the administration method is parenteral administration, the preferable dosage form is a liquid formulation, with which direct administration to the target site, and systemic administration via the circulatory system are possible. A preferable example of a liquid formulation is an injectable. The injectable can be formed to a preparation by mixing it with a solvent in combination with aforementioned excipient, an emulsifier, a suspending agent, a surfactant, a stabilizer, a pH adjuster, etc., as appropriate, in a unit dosage form required in generally accepted pharmaceutical practice.

In a case where the administration method is oral administration, examples of the preferred dosage form include a solid formulation (including tablet, capsule, drop, and lozenge), a granule, a dusting powder, a powder, and a liquid formulation (including mixture for internal use, emulsion formulation, syrup formulations). In the case of a solid formulation, if necessary, a coated dosage form as publicly known in the art, such as a sugar coated tablet, a gelatin coated tablet, an enteric-coated tablet, a film-coated tablet, a double-layered tablet, and a multi-layered tablet, may be used.

There is no particular restriction on the specific shape and size of the respective dosage forms, insofar as those of the relevant dosage form are in the range of those of a publicly known dosage form in the field. In manufacturing the pharmaceutical composition for treating hepatitis B of the present invention, formulation may be performed in accordance with the usual method in the technical field.

2-3. Application Method

The method of application of the pharmaceutical composition for treating hepatitis B of the present invention may be either of oral administration and parenteral administration. In general, the oral administration method is systemic administration, while the parenteral administration method can be further divided into systemic administration and local administration. Examples of the local administration include intramuscular administration, subcutaneous administration, tissue administration, and organ administration, while examples of the systemic administration by the parenteral administration include intracirculatory administration, such as intravenous administration (i.v.), intraarterial administration, and intralymphatic administration. When a pharmaceutical composition for treating hepatitis B of the present invention is locally administered, it may be administered directly to the liver by injection or the like. When it is systemically administered, it may be administered into the circulatory system by intravenous injection, or the like. The dosage may be an amount sufficient for the active ingredient to be effective. As described above, the effective amount is selected appropriately according to the subject information.

The pharmaceutical composition for treating hepatitis B of the present invention may also be used in combination with separately used two or more other publicly known anti-HBV agents.

3. Method for Inhibiting Hepatitis B Virus Replication (Method for Inhibiting HBV Replication)

3-1. Outline

The third aspect of the present invention is a method for inhibiting HBV replication. According to the method for inhibiting HBV replication of the present invention, (I) a peptide fragment constituting a spike region in a core protein of a hepatitis B virus, (II) a peptide fragment in which any amino acid sequence different from the core protein is added to the N-terminus and/or C-terminus of the spike region, or (III) an expression vector comprising a nucleic acid encoding the peptide fragment according to (I) or (II) above, and capable of expressing the peptide fragment in a cell, is introduced into a cell infected with HBV or a cell suspected of infection therewith so that the replication of HBV in the cell is inhibited, thereby inhibiting the replication of HBV, and suppressing the proliferation of HBV. When this method is applied to a patient infected with hepatitis B or a person suspected of infection therewith, it can be a treatment method for hepatitis B.

3-2. Method

The method for inhibiting HBV replication in this aspect comprises an introduction step as an essential step.

The "introduction step" is a step of introducing (I) a peptide fragment constituting a spike region of HBc, (II) a peptide fragment in which any amino acid sequence different from the core protein is added to the N-terminus and/or C-terminus of the spike region, or (III) an expression vector comprising a nucleic acid encoding the peptide fragment according to (I) or (II) above, and capable of expressing the peptide fragment in a cell, namely the inhibitor of HBV replication described in the first aspect into the host.

In this aspect, a "host" refers to a cell, tissue, or individual into which an inhibitor of HBV replication can be introduced. When the host is a cell, the cell may be one or multiple mammalian cells. It is preferably a cell derived from a human or a chimpanzee that is the host of HBV. There is no particular restriction on the type of the derived cell. In addition to a hepatic cell, which is the cell subjected to HBV infection, a cell derived from various organs and tissues can also be the subject. The host can be either a cell line or a primary culture cell line. The host is preferably, but not limited to, a cell infected with HBV or a cell suspected of infection therewith. When the host is an individual, the aforedescribed subject person is preferable.

There is no particular restriction on the method of introducing each expression vector into the host. For example, when the host is a cell or a tissue, a gene introduction method (transfection method) publicly known in the art, such as those described in Green & Sambrook, 2012, Molecular Cloning: A Laboratory Manual Fourth Ed., Cold Spring Harbor Laboratory Press, Cold Spring Harbor, New York, etc. may be used. Examples thereof include a Lipofectin method (PNAS, 1989, 86: 6077; PNAS, 1987, 84: 7413), an electroporation method, a calcium phosphate method (Virology, 1973, 52: 456-467), and a DEAE-dextran method. On the other hand, when the host is an individual, for example a subject person, an inhibitor of HBV replication, or a pharmaceutical composition for treating hepatitis B comprising this inhibitor as the active ingredient may be administered to the subject person according to the method described in "2-3. Application method" of the second aspect. By administering the same to a subject person, the method for inhibiting HBV replication of this aspect can be a method of treating hepatitis B.

EXAMPLES

Example 1: Inhibitory Effect of Mutant HBcs on HBV Replication (Purpose)

Mutant HBcs having various forms of deletion in HBc are produced, and the inhibitory effect on HBV replication is investigated.

(Method)

1. Preparation of Deletion Mutant Forms of HBc

Figure 4:
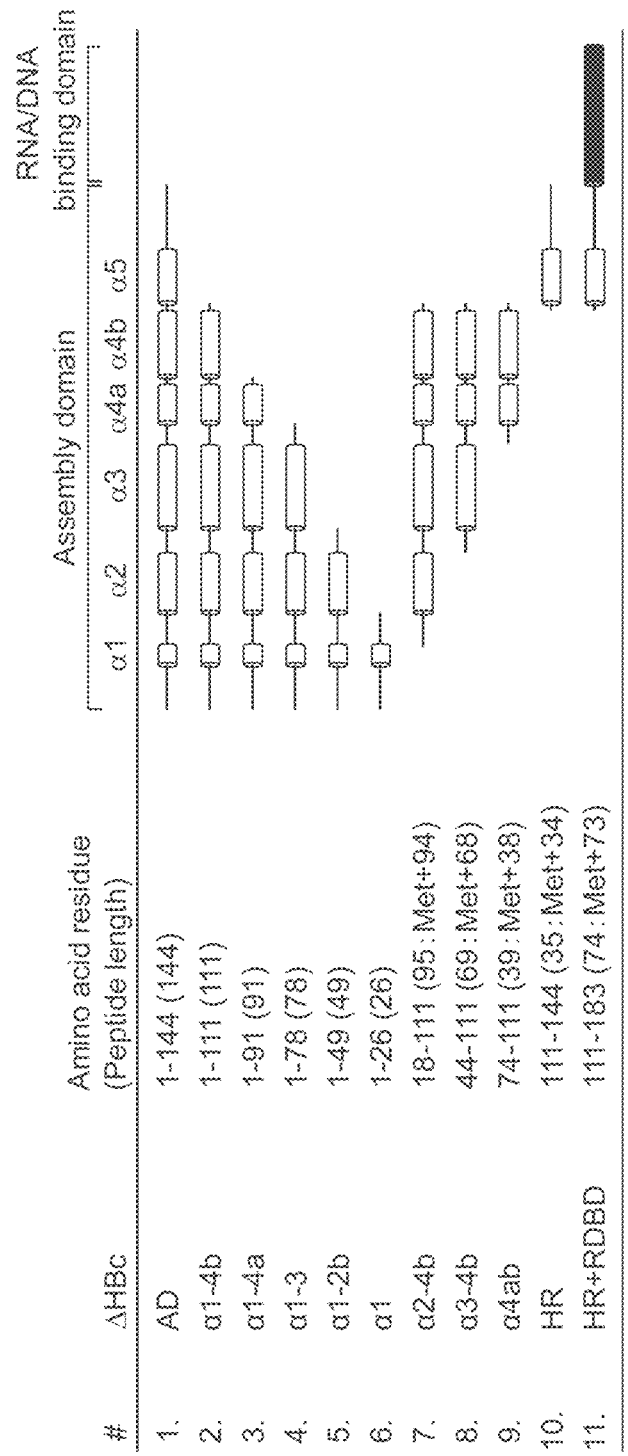
FIG. 4 shows the name of each ΔHBc used in Examples, the amino acid sequence and peptide chain length, as well as domain structure corresponding to each ΔHBc.

The genotype C (HBc/C) of HBc according to the amino acid SEQ ID NO: 16 was determined as the subject of the investigation, and the following 11 types of deletion mutant forms of HBc (ΔHBc) shown in FIG. 4 were prepared.

(1) ΔHBc #1 is a deletion of the RNA/DNA binding domain (RDBD) and is constituted solely by the assembly domain consisting of position 1 to 144 of SEQ ID NO: 16. It is denoted as "AD" in Examples.

(2) ΔHBc #2 consists of position 1 to 111 of SEQ ID NO: 16. It has a structure in which the fifth helix (α5) is deleted from ΔHBc #1 and comprises α1 to α4b. It is denoted as "α1-4b" in Examples. This α1-4b corresponds to the spike region of HBc in which the hand region (HR) is deleted from AD.

(3) ΔHBc #3 consists of position 1 to 91 of SEQ ID NO: 16. It has a structure in which α4b to α5 are deleted from ΔHBc #1, and comprises α1 to α4a. It is denoted as "α1-4a" in Examples.

(4) ΔHBc #4 consists of position 1 to 78 of SEQ ID NO: 16. It has a structure in which α4a to α5 are deleted from ΔHBc #1, and comprises α1 to α3. It is denoted as "α1-3" in Examples.

(5) ΔHBc #5 consists of position 1 to 49 of SEQ ID NO: 16. It has a structure in which α3 to α5 are deleted from ΔHBc #1, and comprises α1 and α2. It is denoted as "α1-2b" in Examples.

(6) ΔHBc #6 consists of position 1 to 26 of SEQ ID NO: 16. It has a structure in which α2 to α5 are deleted from ΔHBc #1, and comprises only α1. It is denoted as "α1" in Examples.

(7) ΔHBc #7 consists of position 1 (initiating methionine) and position 18 to 111 of SEQ ID NO: 16. It has a structure in which α1 and α5 are deleted from ΔHBc #1, and comprises helices α2 to α4b. It is denoted as "α2-4b" in Examples.

(8) ΔHBc #8 consists of position 1 (initiating methionine) and position 44 to 111 of SEQ ID NO: 16. It has a structure in which α1, α2, and α5 are deleted from ΔHBc #1, and comprises α3 to α4b. It is denoted as "α3-4b" in Examples.

(9) ΔHBc #9 consists of position 1 (initiating methionine) and position 74 to 111 of SEQ ID NO: 16. It has a structure in which α1 to α3, and α5 are deleted from ΔHBc #1, and comprises α4a and α4b. It is denoted as "α4ab" in Examples.

(10) ΔHBc #10 consists of position 1 (initiating methionine) and position 111 to 144 of SEQ ID NO: 16. It has a structure in which α1 to α4b are deleted from ΔHBc #1, and comprises only α5. It is denoted as "HR" in Examples. This HR corresponds to the hand region (HR) of HBc where the spike region is deleted from the AD.

(11) ΔHBc #11 consists of position 1 (initiating methionine) and position 111 to 183 of SEQ ID NO: 16. It has a structure in which α1 to α4b are deleted from HBc, and comprises α5 corresponding to the HR and the RNA/DNA binding domain (RDBD). It is denoted as "HR-RDBD" in Examples.

Figure 5:
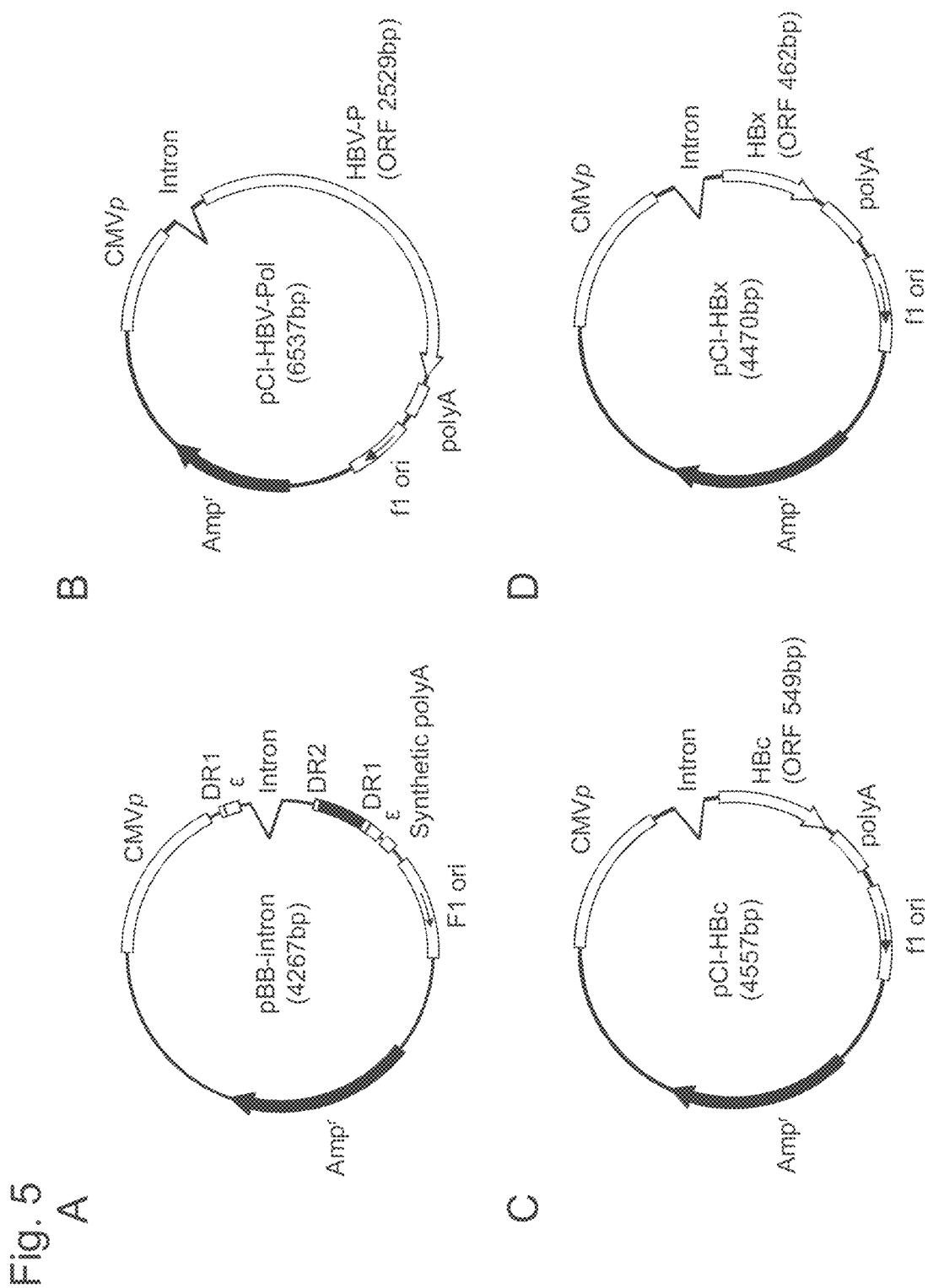
FIG. 5 is schematic diagrams showing examples of various expression vectors constituting the system for evaluating HBV replication activity according to WO2018/030534 used in Examples.

Based on the HBc/C gene shown in SEQ ID NO: 22, in which the codons of the DNA base sequence encoding the full length HBc/C are optimized for a human cell, the region encoding each ΔHBc was cut out and subcloned into the mammalian cell expression vector pCI (Promega) shown in FIG. 5C by a conventional method. The expression vector thus obtained is used as ΔHBc expression vector (pCI-ΔHBc), and for example, a ΔHBc expression vector incorporating α1-4b of ΔHBc #2 is denoted as ΔHBc(α1-4b) expression vector (pCI-ΔHBc(α1-4b)).

2. Effect of ΔHBc on HBV Replication Activity

The effect of each of the aforementioned ΔHBc expression vector (pCI-ΔHBc) on HBV replication was examined using the system for evaluating HBV replication activity described in WO2018/030534 developed by the present inventors.

Specifically, the system for evaluating HBV replication activity consisting of the vector for evaluating HBV replication activity (pBB-intron) encoding the reporter pgRNA shown in FIG. 5A, the HBV-P expression vector (pCI—HBV-Pol) shown in FIG. 5B, the HBc expression vector (pCI-HBc) shown in FIG. 5C, and the HBx expression vector (pCI-HBx) shown in FIG. 5D was introduced into HeLa cells together with each pCI-ΔHBc. The introduction ratio of the respective expression vectors was pBB-intron: pCI-HBc: pCI—HBV-Pol: pCI-HBx: pCI-ΔHBc=13:9:3:1: 26. According to this ratio, the amount of ΔHBc is about three times (2.89 times) as much as that of the wild type HBc functioning in HBV replication. As a positive control, an empty vector (pCI) was introduced at the same ratio as pCI-ΔHBc. For gene introduction into HeLa cells, the electroporation method was used. Using an Electroporator Nepa21 (Nepa Gene Co., Ltd.) 10 µg of DNA was introduced into approximately 1×10$^6$ cells under the condition of 125 V/2.5 ms pulse length. The HeLa cells after gene introduction were cultured in DMEM to which 2 mL of 10% FBS was added in the presence of 5% CO2 at 37° C. for 24 hours.

Figure 6:
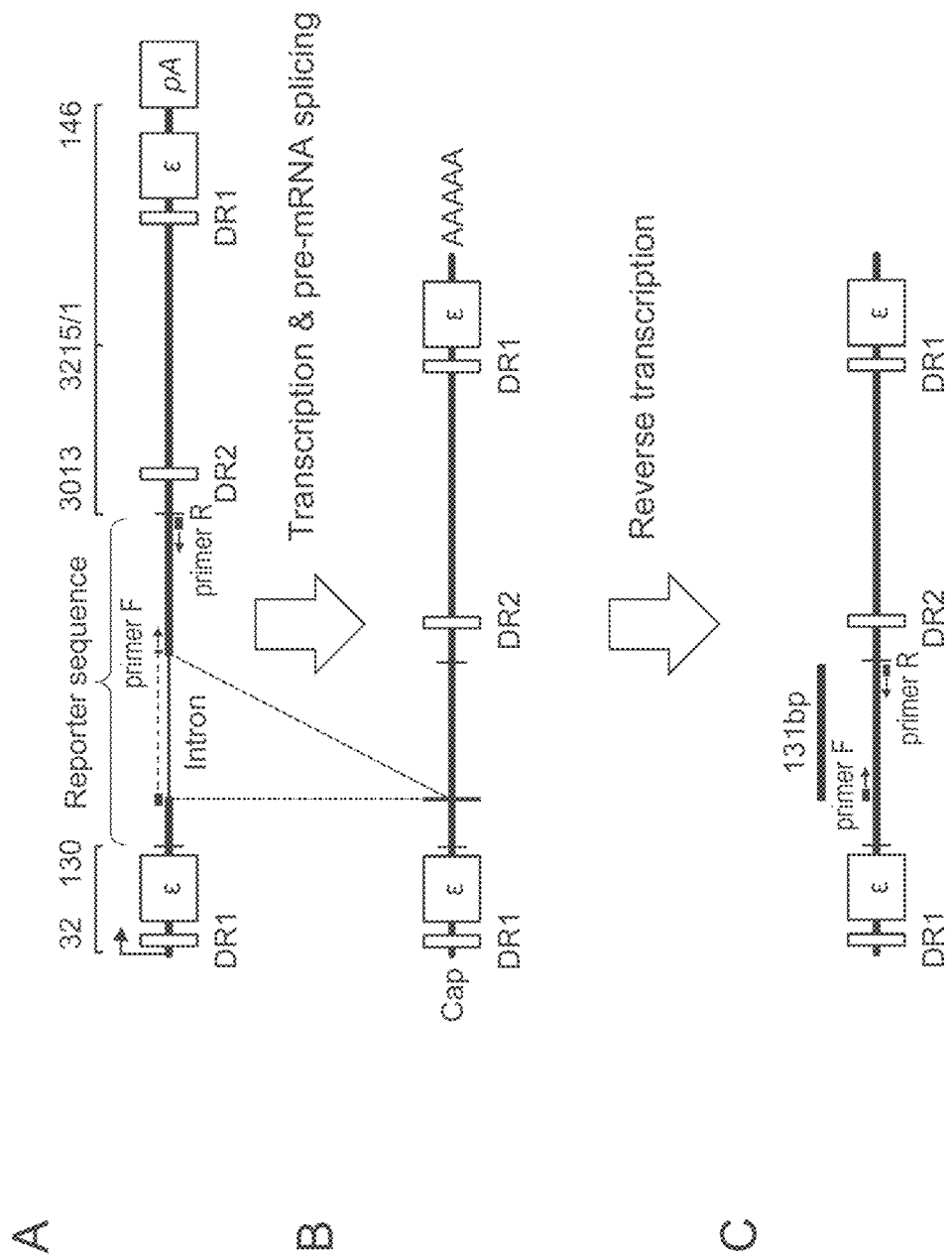
FIG. 6A is a schematic diagram showing an example of a nucleic acid for evaluating HBV replication activity of the present invention.
FIG. 6B is a schematic diagram of reporter pgRNA, expressed after introducing a vector for evaluating HBV replication activity in which the nucleic acid for evaluating HBV replication activity acid shown in FIG. 6A has been incorporated in an expression vector. In the reporter pgRNA, the intron in the reporter sequence has been removed by pre-mRNA splicing.
FIG. 6C is a schematic diagram of reporter (−) DNA synthesized by the reverse transcription activity of HBV-Pol using the reporter pgRNA shown in FIG. 6B as the template. The nucleic acid for evaluating HBV replication activity and the reporter (−) strand DNA can be distinguished by the presence or absence of the intron.

When the vector for evaluating HBV replication activity (pBB-intron) described above is introduced into HeLa cells, pre-mRNA shown in FIG. 6A is synthesized by RNA-pol II in HeLa cells, then an intron comprised in the reporter sequence of pBB-intron is immediately removed by pre-mRNA splicing in HeLa cells. The mature mRNA from which the intron spliced has been spliced out becomes a reporter pgRNA shown in FIG. 6B. The reporter pgRNA is reverse transcribed by the functions of HBV-Pol, HBc, and HBx respectively expressed by the HBV-P expression vector, HBc expression vector, and HBx expression vector, and a reporter minus strand DNA (reporter (−) DNA) comprising the reporter sequence as shown in FIG. 6C, which is different from the reporter sequence of the original vector for evaluating HBV replication activity shown in FIG. 6A, and in which the intron has been removed, is synthesized. The amount of this reporter (−) DNA reflects the replication activity and replication amount of HBV. Therefore, when DNA is extracted from the cells in which the system for evaluating HBV replication activity and pCI-ΔHBc are introduced, the amount thereof is quantified with a primer set specific to the reporter (−) DNA, and then compared with the amount of the positive control, the effect of pCI-ΔHBc on the HBV replication can be evaluated.

DNA was extracted from HeLa cells after culture using DNeasy Mini (Qiagen N.V.). Then, quantitative PCR was performed using a primer set specific to the reporter (−) DNA after reverse transcription. For primers, a forward primer (Primer F) consisting of the base sequence shown in SEQ ID NO: 23, and a reverse primer (Primer R) consisting of the base sequence shown in SEQ ID NO: 24 were used. The Primer F is designed so that the two bases at the 3' end match the two bases at the 5' end of the downstream exon, but do not match the two bases at the 5' end of the intron. Therefore, it functions as a primer only when there is a reporter (−) DNA having the reporter sequence from which the intron has been removed, and the DNA fragment of 131 bases is amplified.

(Results)

Figure 7:
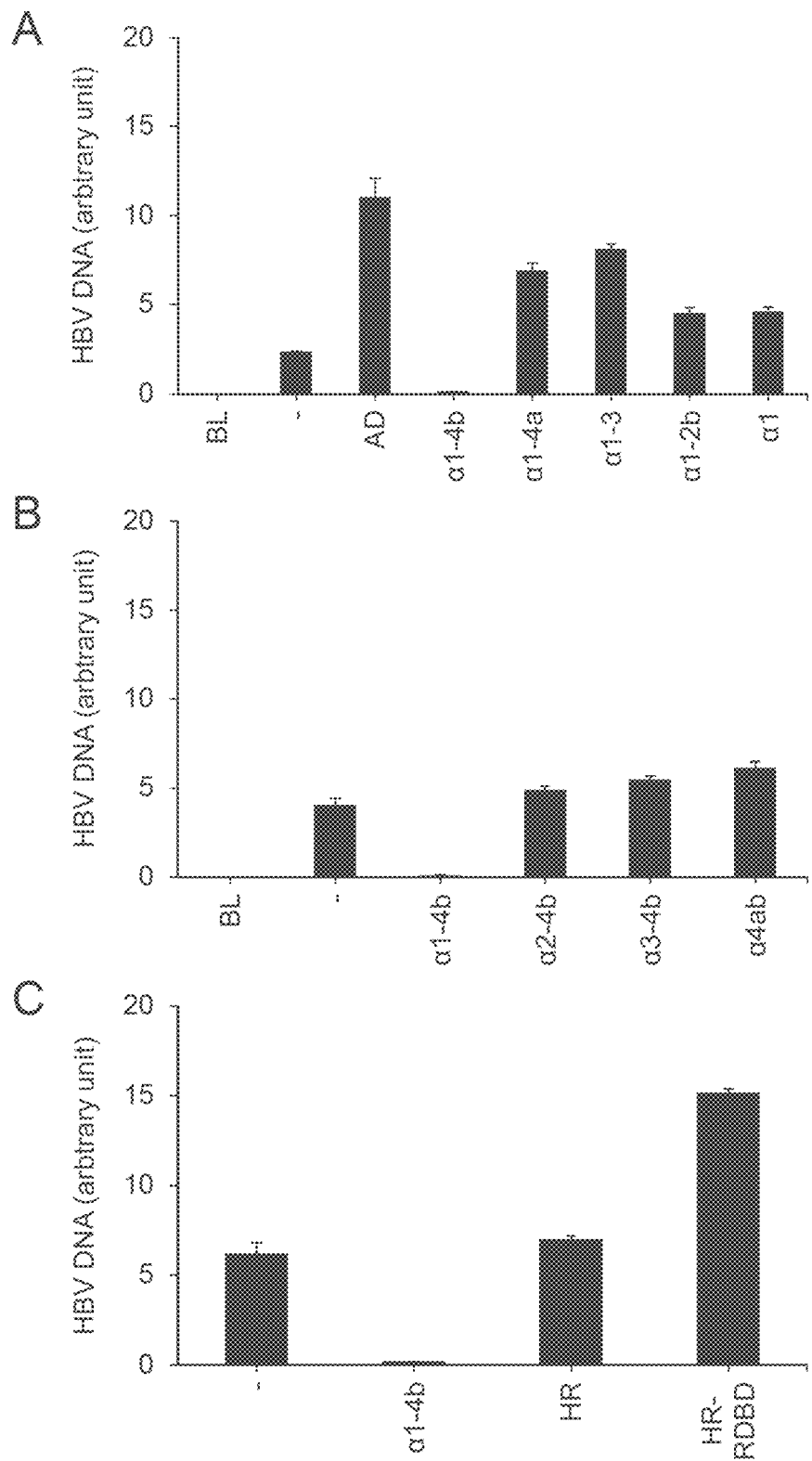
FIG. 7 show the inhibitory effect of ΔHBc on HBV replication.

The results are shown in FIG. 7A to 7C. From these figures, it became clear that replication of HBV was significantly inhibited only in HeLa cells transfected with the spike region designated as α1-4b. On the other hand, the inhibitory activity on HBV replication was lost in ΔHBc (α1-4a, α1-3, α1-2b, and α1) in which the amino acid sequence on the C-terminal side was further deleted from α1-4b in the spike region (FIG. 7A), and ΔHBc (α2-4b, α3-4b, and α4ab) in which the amino acid sequence on the N-terminal side of α1-4b was deleted (FIG. 7B). From these results it has become clear that all α-helices (α1 to α4b) comprised in the spike region are necessary for the inhibitory activity on HBV replication.

Further, very interestingly, even though the assembly domain (AD) comprises all of α1 to 4b, it did not show inhibitory activity on HBV replication, and rather tended to promote HBV replication (FIG. 7A). In addition, when the HR composed only of the hand region was introduced, the effect of inhibitory activity on HBV replication was not observed (FIG. 7C), indicating that the absence of the hand region is important for the inhibitory activity on replication. Furthermore, HR-RDBD also did not show the inhibitory activity on HBV replication (FIG. 7C).

Example 2: Dose-Dependent Effect for Inhibition of HBV Replication by the Spike Region (Purpose)

It is examined whether the spike region inhibits HBV replication in a dose-dependent manner.

(Method)

The basic procedures were in accordance with Example 1. As pCI-ΔHBc to be introduced into HeLa cells together with the system for evaluating HBV replication activity, only pCI-ΔHBc(α1-4b) was used. The introduction ratio of the respective expression vectors was set such that the ratio of pCI-HBc: pCI—HBV-Pol: pCI-HBx was 9:3:1, and the ratio of pBB-intron: pCI-HBc/pCI—HBV-Pol/pCI-HBx was 1:1. Then, only the system for evaluating HBV replication activity in which the ratio of pCI-ΔHBc(α1-4b): pBB-intron/pCI-HBc/pCI—HBV-Pol/pCI-HBx was adjusted to 1:26, 3:26, 9:26, or 26:26, was introduced as a positive control. In each sample, an empty vector (pCI) was used for adjustment so that the amount of the vector to be introduced is the same.
(Results)

Figure 8:
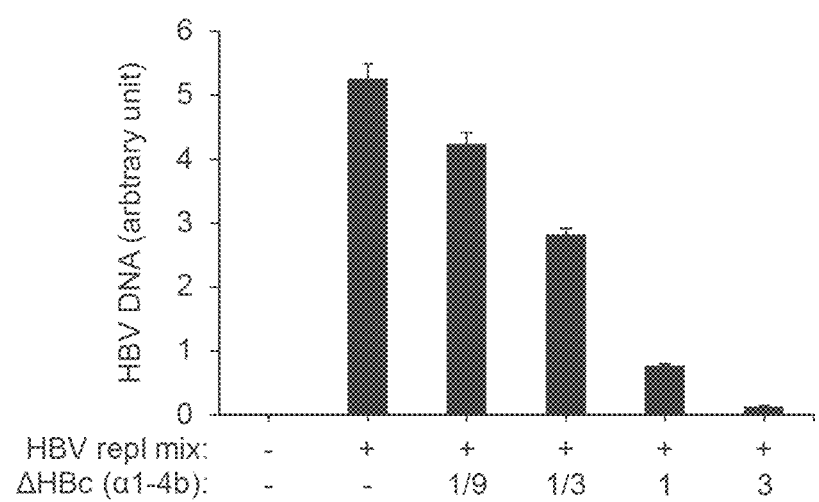
FIG. 8 shows a quantitative inhibitory effect on HBV replication by ΔHBc (α1-4b) corresponding to the spike region of HBc, which showed an inhibitory effect on HBV replication in FIG. 7. A ΔHBc(α1-4b) expression vector was introduced into HeLa cells together with the system for evaluating HBV replication activity. The ΔHBc(α1-4b) was introduced such that the quantitative ratio to the full length wild type HBc expression vector comprised in the system for evaluating HBV replication activity, namely ΔHBc(α1-4b)/WT-HBc, was 1/9, 3/9, 9/9, or 26/9.

The results are shown in FIG. 8. As shown in this figure, it became clear that the replication of HBV was inhibited in a dose-dependent manner by pCI-ΔHBc(α1-4b) introduced, and the replication activity of HBV was substantially lost, when ΔHBc(α1-4b) was introduced in an amount approximately three times (an amount of 26/9) as much as wild-type type HBc. This result indicated that the spike region of HBc inhibited HBV replication depending on its expression level.

Example 3: Inhibitory Effect on HBV Replication Activity by the Spike Region Derived from Each HBc Genotype (Purpose)

There are eight kinds of genotypes of HBc (HBc/A to HBc/H). It is examined whether the inhibitory effect on HBV replication by the spike region of HBc/C, as obtained in Example 1, can also be obtained by the spike regions of other genotypes.
(Method)

The basic procedures were in accordance with Example 1. HBc/A, HBc/D, HBc/E, and HBc/F were used as genotypes other than HBc/C. Since HBc/B had completely the same amino acid sequence as HBc/C, it was used for a control as HBc/B/C.

In order to prepare pCI-ΔHBc(α1-4b) of each genotype, ΔHBc(α1-4b) expression plasmids derived from genotypes A, D, E and F were prepared using pCI-ΔHBc(α1-4b) as the template based on the wild type base sequence information of each genotype of the HBc gene, namely the base sequence of SEQ ID NO: 25 for the HBc/A gene, the base sequence of SEQ ID NO: 26 for the HBc/D gene, the base sequence of SEQ ID NO: 27 for the HBc/E gene, and the base sequence of SEQ ID NO: 28 for the HBc/F gene, and introducing amino acid substitutions by site directed mutagenesis (PrimeSTAR Mutagenesis Basal Kit, Takara Bio Inc.).
(Results)

Figure 9:
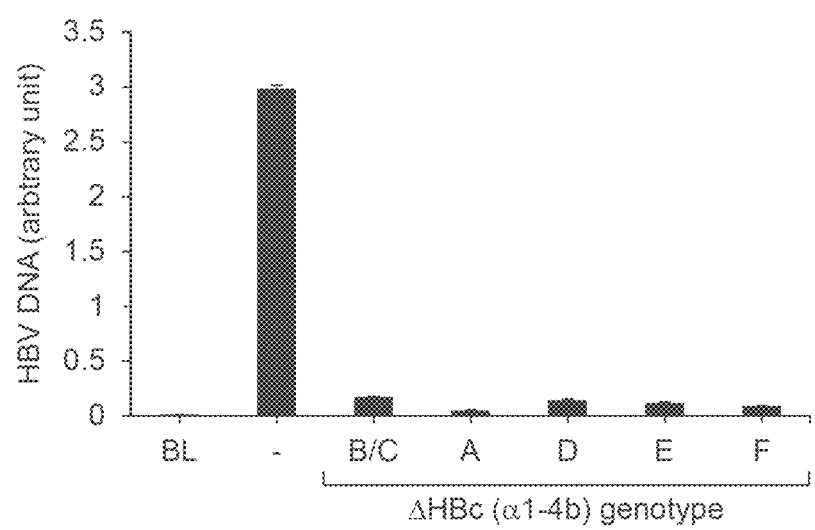
FIG. 9 shows the inhibitory effects of ΔHBc(α1-4b) derived from each genotype on HBV replication.

The results are shown in FIG. 9. As shown in this figure, significant inhibitory activity on HBV replication was observed with respect to the spike regions of all genotypes. This result clearly shows that the spike region of HBc has inhibitory activity on HBV regardless of the genotype.

Example 4: Investigation of Inhibition of HBV Nucleocapsid Formation and Inhibition of HBV Replication by Amino Acid Point Mutations in HBc (Purpose)

It was reported from the structural analysis of HBc, that HBc nucleocapsid formation could be inhibited when phenylalanine (F) at position 23 in the spike region (α1-4b) (position 35 in HBc/G), or leucine (L) at position 42 (position 54 in HBc/G) was respectively substituted with alanine (A) (Alexander C. G., et al., 2013, PNAS, 110 (30): E2782-E2791). Therefore, it is investigated whether these point mutations have an inhibitory effect on nucleocapsid formation and HBV replication.
(Method)
(1) Preparation of HBc Expression Vector Having Introduced F24A or L42A The F residue at position 23, or the L residue at position 42 was respectively substituted with an A residue (denoted as F23A and L42A, respectively) by a site-directed mutagenesis method using PrimeSTAR Mutagenesis Basal Kit (Takara Bio Inc.) using the full length HBc expression vector (pCI-HBc) of genotype C used in Example 1 as the template. The mutants F23A and L42A of the full length HBc having introduced the point mutation are respectively denoted as HBc-F23A and HBc-L42A.
(2) Anti-HBc Monoclonal Antibody An anti-HBc monoclonal antibody for HBc detection in Western blotting, etc was prepared. A peptide shown in SEQ ID NO: 29 (PAYRPPNAPILSTLP) corresponding to position 130 to 144 in the hand region of HBc/C was synthesized, and BALB/c mice (8 weeks old, female) were immunized with the synthetic peptide. Thereafter, a mouse anti-human HBc monoclonal antibody (#511) was prepared by a hybridoma method using the spleen cells of the immunized mice according to the ordinary method.
(3) Western Blotting Each of the expression vectors of the wild type full length HBc (HBc-WT), and mutant full length HBc (HBc-F23A and HBc-L42A) was introduced into HeLa cells, which were cultured for 24 hours. Then proteins were extracted with a WB lysis buffer (1% Triton, 25 mM Tris pH 7.4, 150 mM NaCl). After addition of $CuSO_4$ (100 μM), the protein extract was incubated at room temperature for 20 min, and neutralized with 1 mM EDTA, to which α13-ME-free SDS-PAGE sample buffer was added. Then SDS-PAGE was performed using a 10 to 20% polyacrylamide gel (Super-Sep™ Ace, FUJIFILM Wako Pure Chemical Corporation). After the electrophoresis, the proteins were transferred to a PVDF membrane using a semi-dry blotter, and Western blotting was performed using a mouse anti-human HBc monoclonal antibody (#511).
(4) Particle Blotting Each of the expression vectors of the wild type HBc (HBc-WT), and mutant full length HBc (HBc-F23A and HBc-L42A) was transfected into HeLa cells, which were cultured for 24 hours, and then lysed with a PB lysis buffer (1% $NP_40$, 25 mM Tris pH 7.4, 150 mM NaCl, 1 mM EDTA, 50 mM NaF). The samples were subjected to electrophoresis in a 1.2% agarose (TAE), transferred to a PVDF membrane, and detected using a mouse anti-human HBc monoclonal antibody (#511).
(5) Evaluation of HBV Replication Activity The evaluation of HBV replication activity for HBc having introduced point mutations was performed according to the method described in Example 1. However, the HBc expression vector (pCI-HBc) comprised in the system for evaluating HBV replication described in Example 1 was replaced with HBc-F23A or HBc-L42A in this Example.
(Results)

Figure 10:
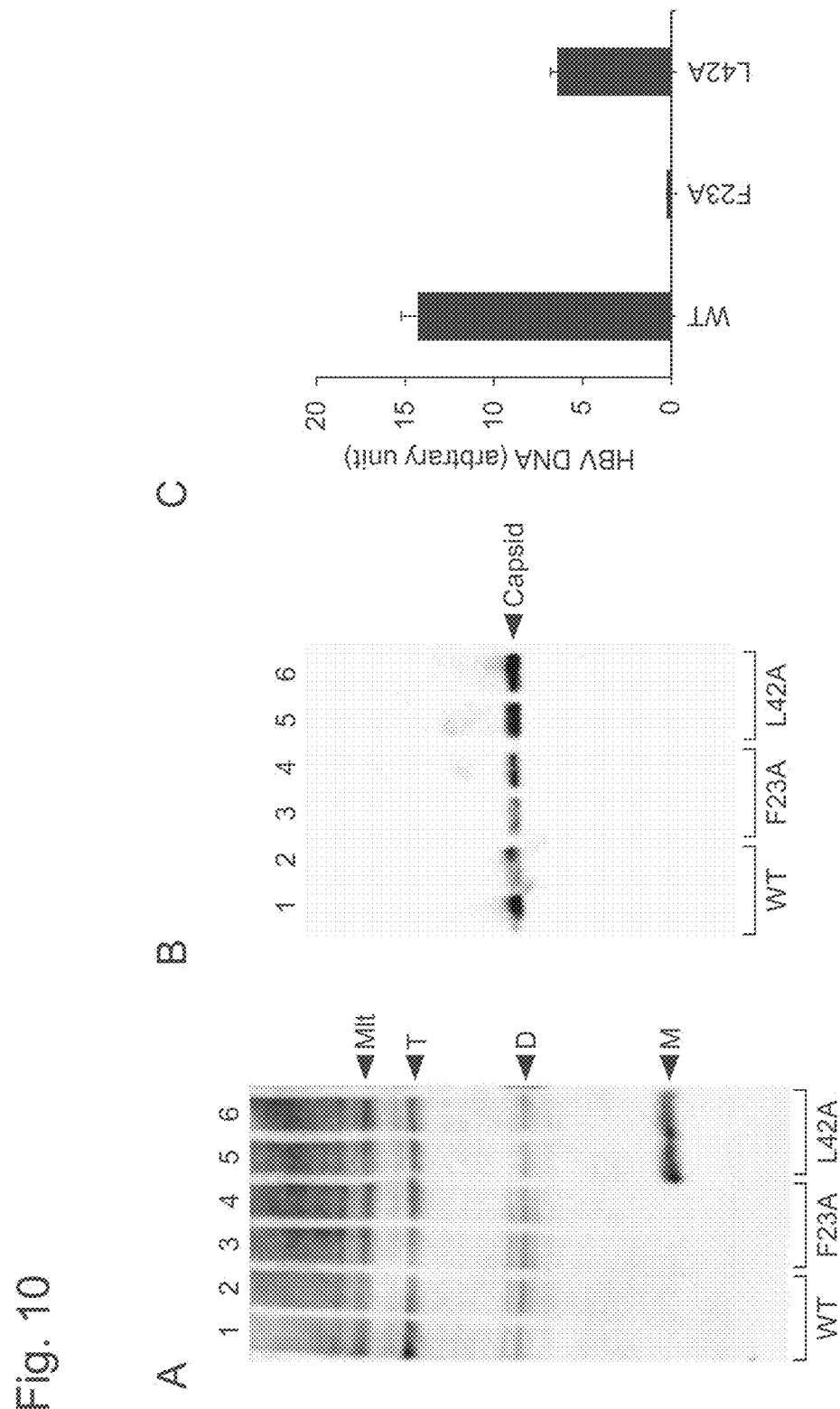
FIG. 10 shows inhibitory effects on HBV nucleocapsid formation and HBV replication by amino acid point mutations in HBc.

The results are shown in FIG. 10. FIG. 10A is the results of Western blotting under non-reducing conditions. In the cells having introduced HBc-WT, there existed substantially no HBc monomer band (M), but intensive bands of multimer (Mlt) of dimer (D) or larger were observed. Also in the cells having introduced HBc-F23A, there existed substantially no monomer (M) similarly to the cells having introduced HBc-WT, and intensive bands of multimer (Mlt) of dimer (D) or larger were observed. These results suggest that the mutation of F23A does not inhibit the multimer forming ability of HBc. On the other hand, in the cells having introduced HBc-L42A, an intensive monomer band (M) was observed, and the dimer band (D) was weakened compared with those in HBc-WT or HBc-F23A. Although this result may suggest that the multimer forming ability is inhibited, the multimer (Mlt) band as intensive as the cells in which HBc-WT or HBc-F23A was introduced was observed. FIG. 10B is the results of particle blotting. The results showed that HBc-WT, HBc-F23A, and HBc-L42A all maintained capsid-forming ability. FIG. 10C is the results of evaluation of inhibitory effects on HBV replication using the system for evaluating HBV replication activity when HBc-F23A or HBc-L42A was introduced into cells in place of HBc-WT. Although HBc-F23A in FIG. 10A showed no significant difference from HBc-WT in terms of multimer forming ability, it was found that HBc-F23A almost completely lost the HBV replication activity. It was found that HBc-L42A retained the replication activity, but the activity was significantly reduced compared to that of HBc-WT. From these results it became clear that introduction of the point mutation of F23A or L42A into the full length wild type HBc affected the inhibitory activity on HBV replication.

Example 5: Investigation of Inhibitory Activity on HBV Replication for Known Amino Acid Mutations that Inhibit HBc Nucleocapsid Formation (Purpose)
It is investigated how introduction of the F23A or L42A mutation into ΔHBc(α1-4b) influences the inhibitory activity of ΔHBc(α1-4b) on HBV replication.
(Method)
(1) Preparation of ΔHBc(α1-4b) Expression Vector Having Introduced F24A or L42A
The F residue at position 23, or the L residue at position 42 was respectively substituted with an A residue (denoted as F23A and L42A, respectively) by a site-directed mutagenesis method using PrimeSTAR Mutagenesis Basal Kit (Takara Bio Inc.) using the ΔHBc(α1-4b) expression vector (pCI-ΔHBc(α1-4b)) of the genotype C used in Example 1 as the template. The ΔHBc(α1-4b) having introduced F23A or L42A are respectively denoted as ΔHBc(α1-4b)-F23A and ΔHBc(α1-4b)-L42A.
(2) Evaluation of HBV Replication Activity
The evaluation of the HBV replication activity of HBc having introduced the point mutation was performed according to the method described in Example 1. In this Example, the wild type pCI-ΔHBc(α1-4b), or the variant having the point mutation, pCI-ΔHBc(α1-4b)-F23A or pCI-ΔHBc(α1-4b)-L42A, was introduced into HeLa cells together with the system for evaluating HBV replication described in Example 1.
Further, for pCI-ΔHBc(α1-4b) and pCI-ΔHBc(α1-4b)-F23A, the plasmids to be introduced were serially diluted with the empty vector (pCI) in the same manner as in Example 2, and the respective dose-dependent effects on the inhibition of HBV replication were investigated.
(Results)
The results are shown in FIG. 11. FIG. 11A shows the results of evaluation of HBV replication activity. From this figure, it was found that the inhibitory effect on HBV replication activity was maintained in either case where pCI-ΔHBc(α1-4b)-F23A or pCI-ΔHBc(α1-4b)-L42A was introduced, but in the cells having introduced pCI-ΔHBc(α1-4b)-L42A, the inhibitory activity on HBV replication was reduced compared to the wild type pCI-ΔHBc(α1-4b). On the other hand, in the cells having introduced pCI-ΔHBc(α1-4b)-F23A, the HBV replication was more strongly inhibited than in the cells having introduced the wild type pCI-ΔHBc(α1-4b). FIG. 11B shows the results of the dose-dependent effect for inhibition of HBV replication. The results showed that ΔHBc(α1-4b)-F23A also inhibited HBV replication depending on its expression level for inhibition similarly to ΔHBc(α1-4b). Further, similarly to the results in FIG. 11A, it was also confirmed that ΔHBc(α1-4b)-F23A had stronger inhibitory activity on HBV replication than ΔHBc(α1-4b).

Example 6: Mechanism of Action for the Inhibition of HBV Replication by the Spike Region ΔHBc(α1-4b)

Figure 12:
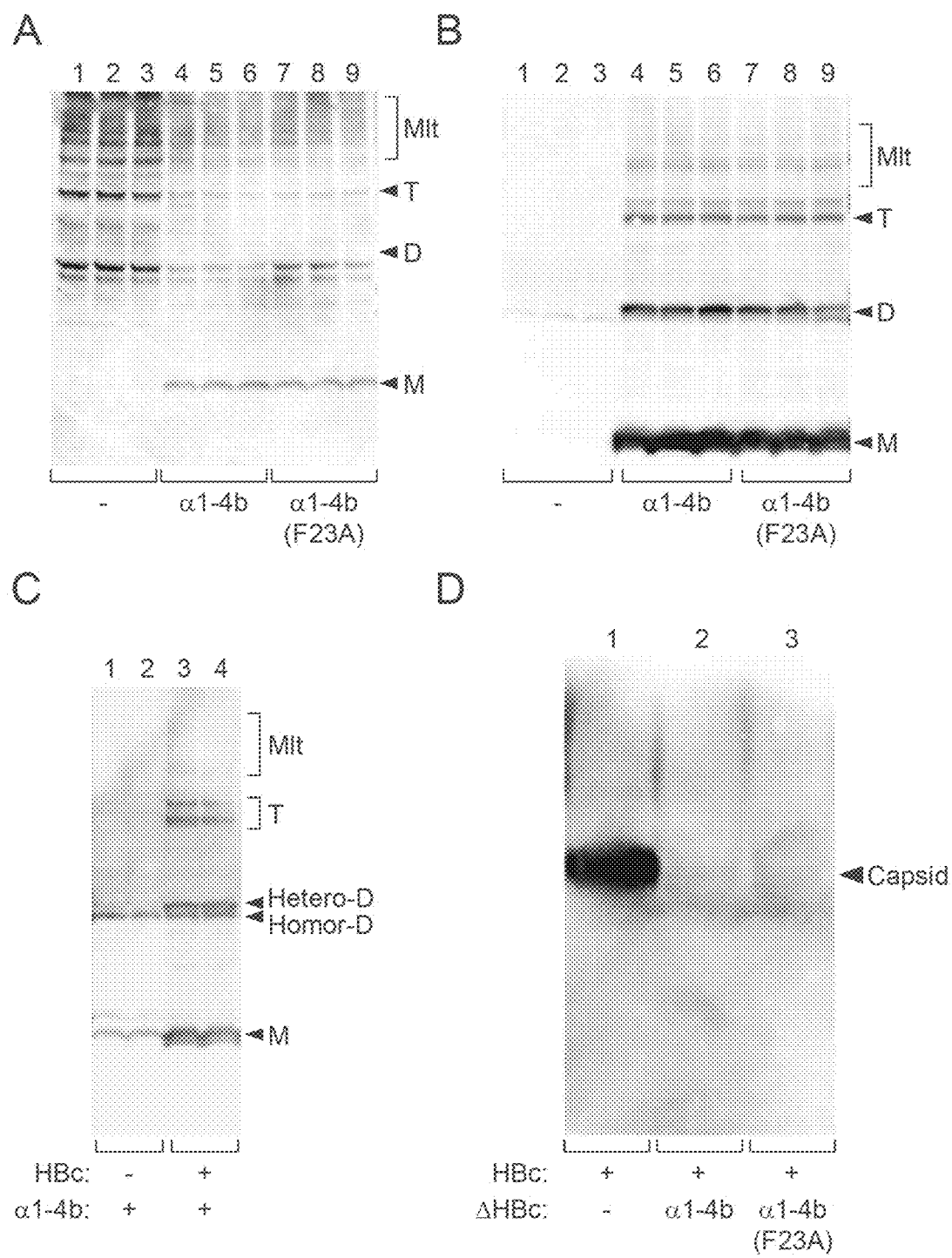
FIG. 12 is diagrams showing the inhibitory effect of ΔHBc(α1-4b) or ΔHBc(α1-4b)-F23A on HBc multimer formation, and its inhibitory effect on nucleocapsid formation of HBc.

(Purpose)
The mechanism of action for the inhibition of HBV replication by the spike region ΔHBc(α1-4b) is investigated.
(Method)
(1) Preparation of Tagged ΔHBc Expression Vector.
Using the wild type or F23A mutant ΔHBc(α1-4b) expression vector (pCI-ΔHBc(α1-4b) and pCI-ΔHBc(α1-4b)-F23A, respectively), a nucleic acid fragment encoding a PA tag (GVAMPGAEDDVV) consisting of 12 amino acid residues shown in SEQ ID NO: 30 was inserted to the C-terminus of each ΔHBc(α1-4b). The resulting tagged ΔHBc expression vectors were denoted as pCI-ΔHBc(α1-4b)-PA and pCI-ΔHBc(α1-4b)-F23A-PA.
(2) HBV Replication Assay
The inhibitory activity on HBV replication of pCI-ΔHBc(α1-4b)-PA and pCI-ΔHBc(α1-4b)-F23A-PA was evaluated using the system for evaluating HBV replication activity described in Example 1. The cell transfection ratio of the system for evaluating HBV replication activity to the ΔHBc expression vector was determined as 26:26. The results showed that inhibitory activity on HBV replication was maintained even when the PA tag was added to the C-terminus of ΔHBc(α1-4b) or ΔHBc(α1-4b)-F23A (figures not shown).
(3) Western Blotting
The basic procedures were in accordance with the method described in Example 4. pCI-ΔHBc(α1-4b)-PA alone, or pCI-ΔHBc(α1-4b)-PA and pCI-ΔHBc(α1-4b)-F23A-PA at a ratio of 1:1 were introduced into HeLa cells. For detecting ΔHBc, the anti-HBc monoclonal antibody #511 described in Example 4 and the anti-PA monoclonal antibody NZ-1 (FUJIFILM Wako Pure Chemical Corporation) were used. Since the anti-HBc monoclonal antibody #511 recognizes the hand region of HBc, it recognizes in this case only the full length HBc and does not recognize ΔHBc(α1-4b)-PA and ΔHBc(α1-4b)-F23A-PA in which the hand region is deleted. On the other hand, the anti-PA monoclonal antibody NZ-1 recognizes the PA tag, it recognizes only ΔHBc(α1-4b)-PA and ΔHBc(α1-4b)-F23A-PA, but does not recognize the full length HBc without the PA tag.
(4) Particle Blotting
The basic procedures were in accordance with the method described in Example 4. The introduction ratio of pCI-ΔHBc(α1-4b)-PA to pCI-ΔHBc(α1-4b)-F23A-PA was determined as 1:3. After culturing for 24 hours, HeLa cells were lysed with 300 μL of THE buffer (10 mM Tris pH 8.0, 100 mM NaCl, and 1 mM EDTA). 100 μL of 4×PNE buffer (26% PEG 8000, 1.4 M NaCl, and 40 mM EDTA) was added to the sample. After incubation on ice for 2 hours, the sample was centrifuged at 15,000 rpm, 4° C., for 15 min, and then subjected to particle blotting by the method described in Example 4.
(Results)
The results are shown in FIG. 12. FIG. 12A shows the results of analysis of the influence of expression of PA-tagged ΔHBc(α1-4b) or ΔHBc(α1-4b)-F23A on HBc dimer formation and multimer formation performed by Western blotting using the anti-HBc monoclonal antibody #511. The results show that in cells in which only full length HBc was expressed (lanes 1 to 3), the full length HBc was present as multimer (Mlt) of dimer (D) or larger, and a monomer (M) was almost not detectable. On the other hand, in cells in which the full length HBc as well as ΔHBc(α1-4b)-PA (lanes 4 to 6) or ΔHBc(α1-4b)-F23A-PA (lanes 7 to 9) were coexpressed, not only the dimer (D) of the full length HBc but also multimer (Mlt) of tetramer (T) or larger were reduced, while a large amount of monomer (M) was detected. These results suggested that ΔHBc(α1-4b) and ΔHBc(α1-4b)-F23A inhibited the normal multimer formation of the full length HBc. FIG. 12B shows the results of analysis of the influence of expression of ΔHBc(α1-4b) or ΔHBc(α1-4b)-F23A on HBc dimer formation and multimer formation performed by Western blotting, similarly to FIG. 12A, using the anti-PA monoclonal antibody NZ-1. Unlike FIG. 12A, NZ-1 did not recognize the full length HBc without PA tag (lanes 1 to 3). On the other hand, in the cases of ΔHBc(α1-4b)-PA (lanes 4 to 6) and ΔHBc(α1-4b)-F23A-PA (lanes 7 to 9), a small amount of tetramer (T) or larger in addition to the dimer (D) was detected, but the amount of the monomer (M) was overwhelming FIG. 12C shows the results of analysis by Western blotting using the NZ-1 antibody after expression of ΔHBc(α1-4b)-PA alone, or co-expression with full length HBc in Hela cells. It was shown that ΔHBc(α1-4b) existed as monomer (M) or homodimer (Homo-D), and did not form a multimer not smaller than tetramer (T). On the other hand, in HeLa cells in which the full length HBc and ΔHBc (α1-4b) were coexpressed, tetramer (T) and multimer (Mlt) were also detected, as in the results of FIG. 12B, and dimers appeared in two bands. One of these bands was located at the same position as that of the homodimer of ΔHBc(α1-4b), while the other band was located above it. Thus, it was suggested that when the full length HBc and the ΔHBc(α1-4b) were coexpressed, the ΔHBc(α1-4b) formed a heterodimer (Hetero-D) with the full length HBc. Although the ΔHBc(α1-4b) alone does not form a complex larger than a dimer, it was revealed that it forms a complex of a tetramer or larger with the wild-type HBc when coexpressed with the wild-type HBc. FIG. 12D shows from the results of particle blotting that expression of α1-4b inhibits capsid formation. From these results it was revealed that the ΔHBc(α1-4b) expressed in a cell, namely the spike region of HBc, forms a heterodimer with a functional full length HBc, inhibits subsequent formation of multimer and formation of capsid, and thereby inhibits HBV replication.

Example 7: Investigation of Resistance of HBc Having T33N Mutation to the Inhibitor of Nucleocapsid Formation GLS4

(Purpose)

It was reported that HBc with T33N mutation (HBc-T33N) showed strong resistance to an inhibitor of nucleocapsid formation composed of existing small molecule compounds (Zhou Z., et al., 2017, Sci Rep, 2017 Feb. 13, 7: 42374). Therefore, it is investigated whether the resistance to the inhibitor of nucleocapsid formation GLS4 composed of small molecule compounds is exhibited when replication of a virus resistant to an inhibitor of nucleocapsid formation is reproduced by using HBc-T33N instead of HBc-WT in the system for evaluating HBV replication activity.

(Method)

(1) Preparation of HBc Expression Vector Having Introduced T33N Mutation

The T residue at position 33 was substituted with an N residue (denoted as T33N) by a site-directed mutagenesis method using PrimeSTAR Mutagenesis Basal Kit (Takara Bio Inc.) using the full length HBc expression vector (pCI-HBc) of genotype C used in Example 1 as the template. The T33N mutant of the full length HBc having introduced the point mutation is denoted as HBc-T33N.

(2) Evaluation of Efficiency for Inhibition of HBV Replication

The measurement of the HBV replication activity by HBc-WT or HBc-T33N was performed in accordance with the method described in Example 1 using HBc-WT or HBc-T33N as HBc comprised in the system for evaluating HBV replication described in Example 1 in the presence of GLS4 at a concentration of 0 μM, 0.08 μM, 0.16 μM, 0.31 μM, 0.63 μM, 1.25 μM, 2.5 μM, or 5 μM. Based on the obtained measurement value of HBV replication activity (amount of reverse transcribed HBV DNA), the efficiency for inhibition of HBV replication (%) was calculated. The efficiency for inhibition of HBV replication (%) in the presence of a particular concentration of GLS4 is calculated by assuming the amount of reverse transcribed HBV DNA at the GLS4 concentration of 0 μM (GLS4 not added) as "0% inhibition", and the amount of reverse transcribed HBV DNA of 0 (the case where reverse transcription did not occur at all) as "100% inhibition."

(Results)

Figure 13:
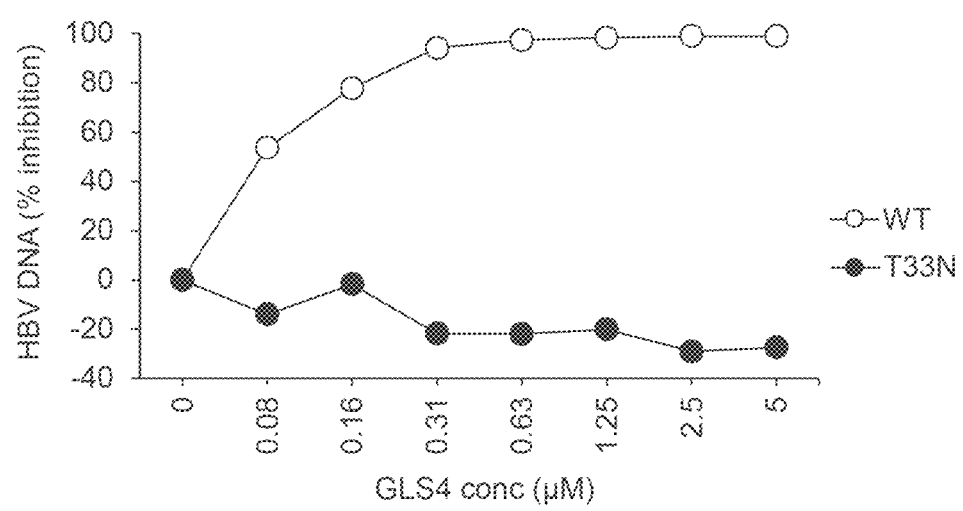
FIG. 13 shows the quantitative inhibitory effect of a nucleocapsid formation inhibitor GLS4 on HBV replication. As the HBc to be included in the system for evaluating HBV replication activity, a wild type HBc (HBc-WT), or HBc (HBc-T33N) having introduced T33N mutation in place of the wild type HBc was used. The vertical axis of the graph shows the efficiency of inhibition on HBV replication. The efficiency of inhibition on HBV replication in the presence of a certain concentration of GLS4 is calculated based on the measured value of HBV replication activity at that concentration by assuming the HBV replication activity when the GLS4 concentration is 0 μM as "0% inhibition", and when the HBV replication activity is 0 as "100% inhibition".

FIG. 13 shows the results of the investigation in which HBc-WT, or HBc-T33N in place of HBc-WT in the system for evaluating HBV replication activity was introduced into cells, and the inhibitory effect on HBV replication in the presence of various concentrations of GLS4 was investigated. GLS4 inhibited HBV replication by HBc-WT in a concentration-dependent manner, while it did not exhibit inhibitory effect on HBV replication by HBc-T33N, indicating that HBc-T33N is resistant to GLS4. This result showed that replication of a virus resistant to an inhibitor of nucleocapsid formation is reproduced by using HBc-T33N in place of HBc-WT in the system for evaluating HBV replication activity.

Example 8: Investigation of Inhibitory Effect of the Spike Region ΔHBc(α1-4b) on HBV Replication by HBc-T33N (Purpose)

It is investigated whether the spike region ΔHBc(α1-4b) inhibits HBV replication by a mutant HBc (HBc-T33N) resistant to an inhibitor of nucleocapsid formation.

(Method and Results)

The evaluation of the inhibitory effect on HBV replication of the spike region ΔHBc(α1-4b) was in accordance with the method described in Example 2. However, in this Example, HBc-WT or HBc-T33N was used as the HBc comprised in the system for evaluating HBV replication described in Example 2.

(Results)

Figure 14:
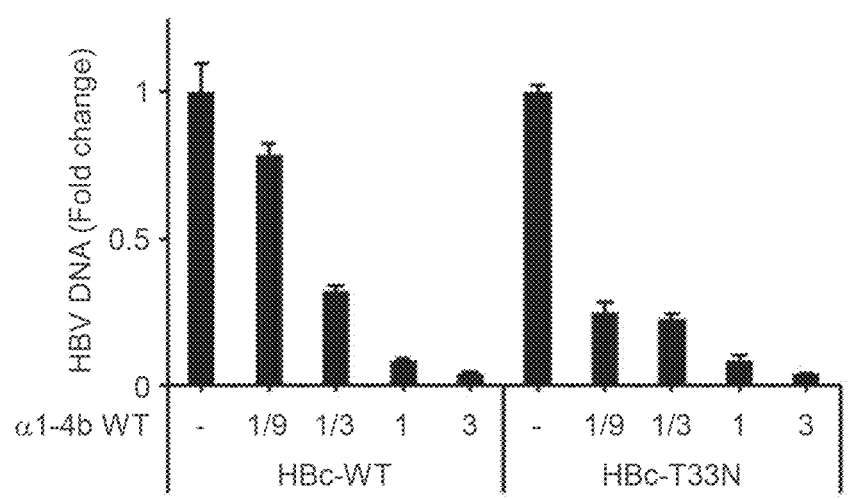
FIG. 14 shows the quantitative inhibitory effect of ΔHBc (α1-4b) on HBV replication. As the HBc to be comprised in the system for evaluating HBV replication activity, the wild type HBc (HBc-WT), or HBc-T33N in place of HBc-WT was used. A ΔHBc(α1-4b) expression vector was introduced together with the system for evaluating HBV replication activity into HeLa cells. The ΔHBc(α1-4b) was introduced such that the quantitative ratio to HBc-WT or HBc-T33N comprised in the system for evaluating HBV replication activity, namely ΔHBc(α1-4b)/(HBc-WT) or ΔHBc(α1-4b)/ (HBc-T33N), was 1/9, 3/9, 9/9, or 26/9. The vertical axis of the graph shows the relative HBV replication activity assuming the replication activity when the ΔHBc(α1-4b) was not introduced as 1.

The results are shown in FIG. 14. The wild type ΔHBc (α1-4b) inhibited HBV replication by HBc-WT (FIG. 14, left) in a dose-dependent manner, and similarly inhibited HBV replication by HBc-T33N in a dose-dependent manner (FIG. 14, right). This result showed that the spike region ΔHBc(α1-4b) had inhibitory effect on HBV replication also with respect to HBc-T33N, which showed GLS4 resistance in Example 7.

All publication, patents and patent applications cited herein are incorporated herein by reference without modification.

The invention claimed is:

1. A method for inhibiting hepatitis B virus replication comprising introducing into a host a peptide fragment constituting a spike region in a core protein of a hepatitis B virus:
wherein said peptide fragment constituting the spike region consists of the amino acid sequence corresponding to SEQ ID NO: 2.

2. The method according to claim 1, further comprising introducing an anti-hepatitis B virus agent to the host.

3. The method according to claim 2, wherein the anti-hepatitis B virus agent is a nucleic acid analog and/or an HBV-Pol activity inhibitor.

* * * * *

```
                        SEQUENCE LISTING

<160> NUMBER OF SEQ ID NOS: 30

<210> SEQ ID NO 1
<211> LENGTH: 111
<212> TYPE: PRT
<213> ORGANISM: hepatitis B virus

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly
            100                 105                 110

<210> SEQ ID NO 2
<211> LENGTH: 111
<212> TYPE: PRT
<213> ORGANISM: hepatitis B virus

<400> SEQUENCE: 2

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly
            100                 105                 110

<210> SEQ ID NO 3
<211> LENGTH: 111
<212> TYPE: PRT
<213> ORGANISM: hepatitis B virus

<400> SEQUENCE: 3

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30
```

```
Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Thr Leu Ala Thr Trp Val Gly Gly Asn Leu Glu Asp Pro Ile
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly
            100                 105                 110
```

<210> SEQ ID NO 4
<211> LENGTH: 111
<212> TYPE: PRT
<213> ORGANISM: hepatitis B virus

<400> SEQUENCE: 4

```
Met Asp Ile Asp Pro Tyr Lys Glu Phe Gly Ala Thr Val Glu Leu Leu
 1                   5                  10                  15

Ser Phe Leu Pro Ser Asp Phe Pro Ser Val Arg Asp Leu Leu Asp
                 20                  25                  30

Thr Ala Ser Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Thr Leu Ala Thr Trp Val Gly Val Asn Leu Glu Asp Pro Ala
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly
            100                 105                 110
```

<210> SEQ ID NO 5
<211> LENGTH: 111
<212> TYPE: PRT
<213> ORGANISM: hepatitis B virus

<400> SEQUENCE: 5

```
Met Asp Ile Asp Pro Tyr Lys Glu Phe Gly Ala Ser Val Glu Leu Leu
 1                   5                  10                  15

Ser Phe Leu Pro Ser Asp Phe Pro Ser Val Arg Asp Leu Leu Asp
                 20                  25                  30

Thr Ala Ser Ala Leu Tyr Arg Asp Ala Leu Glu Ser Pro Glu His Cys
            35                  40                  45

Thr Pro Asn His Thr Ala Leu Arg Gln Ala Ile Leu Cys Trp Gly Glu
 50                  55                  60

Leu Met Thr Leu Ala Ser Trp Val Gly Asn Asn Leu Glu Asp Pro Ala
 65                  70                  75                  80

Ala Arg Asp Leu Val Val Asn Tyr Val Asn Thr His Met Gly Leu Lys
                 85                  90                  95

Ile Arg Gln Leu Leu Trp Phe His Ile Ser Cys Leu Thr Phe Gly
            100                 105                 110
```

<210> SEQ ID NO 6
<211> LENGTH: 111
<212> TYPE: PRT
<213> ORGANISM: hepatitis B virus

<400> SEQUENCE: 6

Met Asp Ile Asp Pro Tyr Lys Glu Phe Gly Ala Ser Ala Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Thr Pro Asn His Thr Ala Leu Arg Gln Ala Ile Leu Cys Trp Gly Glu
        50                  55                  60

Leu Met Thr Leu Ala Ser Trp Val Gly Asn Asn Leu Gln Asp Pro Ala
65                  70                  75                  80

Ala Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly
            100                 105                 110

<210> SEQ ID NO 7
<211> LENGTH: 123
<212> TYPE: PRT
<213> ORGANISM: hepatitis B virus

<400> SEQUENCE: 7

Met Asp Arg Thr Thr Leu Pro Tyr Gly Leu Phe Gly Leu Asp Ile Asp
1               5                   10                  15

Pro Tyr Lys Glu Phe Gly Ala Thr Val Glu Leu Leu Ser Phe Leu Pro
                20                  25                  30

Ser Asp Phe Phe Pro Ser Val Arg Asp Leu Leu Asp Thr Ala Ser Ala
            35                  40                  45

Leu Tyr Arg Glu Ser Leu Glu Ser Ser Asp His Cys Ser Pro His His
        50                  55                  60

Thr Ala Leu Arg Gln Ala Ile Leu Cys Trp Gly Glu Leu Met Thr Leu
65                  70                  75                  80

Ala Thr Trp Val Gly Asn Asn Leu Glu Asp Pro Ala Ser Arg Asp Leu
                85                  90                  95

Val Val Asn Tyr Val Asn Thr Asn Met Gly Leu Lys Ile Arg Gln Leu
            100                 105                 110

Leu Trp Phe His Ile Ser Cys Leu Thr Phe Gly
        115                 120

<210> SEQ ID NO 8
<211> LENGTH: 336
<212> TYPE: DNA
<213> ORGANISM: hepatitis B virus

<400> SEQUENCE: 8
atggacatcg acccctacaa agaattcggc gccaccgtgg aactgctgag cttcctgccc    60
agcgacttct cccctccgt gcgggacctg ctggatacag ccagcgccct gtatagagag    120
gccctggaaa gccccgagca ctgcagccct catcacaccg ctctgagaca ggccatcctg    180
tgctggggcg agctgatgac cctggccacc tgggtgggaa acaacctgga agatcccgcc    240
agccgggacc tggtggtgaa ctacgtgaac accaacatgg gcctgaagat ccggcagctg    300
ctgtggttcc acatctcctg cctgaccttc ggctga                              336

<210> SEQ ID NO 9
<211> LENGTH: 336
<212> TYPE: DNA

<213> ORGANISM: hepatitis B virus

<400> SEQUENCE: 9

```
atggacatcg acccctacaa agaattcggc gccagcgtgg aactgctgag cttcctgccc      60
agcgacttct tcccctccat ccgggacctg ctggatacag ccagcgccct gtatagagag     120
gccctggaaa gccccgagca ctgcagccct catcacaccg ctctgagaca ggccatcctg     180
tgctggggcg agctgatgaa tctggccacc tgggtgggaa gcaacctgga agatcccgcc     240
agccgggaac tggtggtgtc ctacgtgaac gtgaacatgg gcctgaagat ccggcagctg     300
ctgtggttcc acatctcctg cctgaccttc ggctga                               336
```

<210> SEQ ID NO 10
<211> LENGTH: 336
<212> TYPE: DNA
<213> ORGANISM: hepatitis B virus

<400> SEQUENCE: 10

```
atggacatcg acccctacaa agaattcggc gccaccgtgg aactgctgag cttcctgccc      60
agcgacttct tcccctccgt gcgggacctg ctggatacag ccagcgccct gtatagagag     120
gccctggaaa gccccgagca ctgcagccct catcacaccg ctctgagaca ggccatcctg     180
tgctggggcg agctgatgac cctggccacc tgggtgggag gcaacctgga agatcccatc     240
agccgggacc tggtggtgtc ctacgtgaac accaacatgg gcctgaagtt ccggcagctg     300
ctgtggttcc acatctcctg cctgaccttc ggctga                               336
```

<210> SEQ ID NO 11
<211> LENGTH: 336
<212> TYPE: DNA
<213> ORGANISM: hepatitis B virus

<400> SEQUENCE: 11

```
atggacatcg acccctacaa agaattcggc gccaccgtgg aactgctgag cttcctgccc      60
agcgacttct tcccctccgt gcgggacctg ctggatacag ccagcgccct gtatagagac     120
gccctggaaa gccccgagca ctgcagccct catcacaccg ctctgagaca ggccatcctg     180
tgctggggcg agctgatgac cctggccacc tgggtgggag tgaacctgga agatcccgcc     240
agccgggacc tggtggtgtc ctacgtgaac accaacatgg gcctgaagtt ccggcagctg     300
ctgtggttcc acatctcctg cctgaccttc ggctga                               336
```

<210> SEQ ID NO 12
<211> LENGTH: 336
<212> TYPE: DNA
<213> ORGANISM: hepatitis B virus

<400> SEQUENCE: 12

```
atggacatcg acccctacaa agaattcggc gccagcgtgg aactgctgag cttcctgccc      60
agcgacttct tcccctccgt gcgggacctg ctggatacag ccagcgccct gtatagagac     120
gccctggaaa gccccgagca ctgcaccccT aaccacaccg ctctgagaca ggccatcctg     180
tgctggggcg agctgatgac cctggccagc tgggtgggaa acaacctgga agatcccgcc     240
gcccgggacc tggtggtgaa ctacgtgaac acccacatgg gcctgaagat ccggcagctg     300
ctgtggttcc acatctcctg cctgaccttc ggctga                               336
```

<210> SEQ ID NO 13
<211> LENGTH: 336

```
<212> TYPE: DNA
<213> ORGANISM: hepatitis B virus

<400> SEQUENCE: 13
atggacatcg accctacaa agaattcggc gccagcgccg aactgctgag cttcctgccc      60
agcgacttct tccctccgt gcgggacctg ctggatacag ccagcgccct gtatagagag     120
gccctggaaa gccccgagca ctgcacacct aaccacaccg ctctgagaca ggccatcctg    180
tgctggggcg agctgatgac actggccagc tgggtgggaa acaacctgca ggatcccgcc    240
gcccgggatc tggtggtgaa ctacgtgaac acaaacatgg gcctgaagat ccggcagctg    300
ctgtggttcc acatctcctg cctgaccttc ggctga                              336

<210> SEQ ID NO 14
<211> LENGTH: 372
<212> TYPE: DNA
<213> ORGANISM: hepatitis B virus

<400> SEQUENCE: 14
atggaccgga ccaccctgcc ctacggcctg ttcggcctgg acatcgaccc ctacaaagaa     60
ttcggcgcca cagtggaact gctgagcttc ctgcccagcg acttcttccc ctccgtccgg    120
gacctgctgg atacagccag cgccctgtat agagagagcc tggaaagcag cgatcactgc    180
agccctcatc acaccgctct gagacaggcc atcctgtgct ggggcgagct gatgaccctg    240
gccacctggg tggaaacaa cctggaagat cccgccagcc gggacctggt ggtgaactac    300
gtgaacacca acatgggcct gaagatccgg cagctgctgt ggttccacat ctcctgcctg    360
accttcggct ga                                                       372

<210> SEQ ID NO 15
<211> LENGTH: 185
<212> TYPE: PRT
<213> ORGANISM: hepatitis B virus

<400> SEQUENCE: 15

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175
```

```
Arg Ser Gln Ser Arg Glu Ser Gln Cys
            180                 185

<210> SEQ ID NO 16
<211> LENGTH: 183
<212> TYPE: PRT
<213> ORGANISM: hepatitis B virus

<400> SEQUENCE: 16

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 17
<211> LENGTH: 183
<212> TYPE: PRT
<213> ORGANISM: hepatitis B virus

<400> SEQUENCE: 17

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125
```

-continued

```
Pro Pro Ala Tyr Arg Pro Pro Asn Ala Pro Ile Leu Ser Thr Leu Pro
        130                 135                 140
Glu Thr Thr Val Val Arg Arg Gly Arg Ser Pro Arg Arg Arg Thr
145                 150                 155                 160
Pro Ser Pro Arg Arg Arg Arg Ser Gln Ser Pro Arg Arg Arg Ser
                165                 170                 175
Gln Ser Arg Glu Ser Gln Cys
            180

<210> SEQ ID NO 18
<211> LENGTH: 183
<212> TYPE: PRT
<213> ORGANISM: hepatitis B virus

<400> SEQUENCE: 18

Met Asp Ile Asp Pro Tyr Lys Glu Phe Gly Ala Thr Val Glu Leu Leu
1               5                   10                  15
Ser Phe Leu Pro Ser Asp Phe Phe Pro Ser Val Arg Asp Leu Leu Asp
            20                  25                  30
Thr Ala Ser Ala Leu Tyr Arg Asp Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Thr Leu Ala Thr Trp Val Gly Val Asn Leu Glu Asp Pro Ala
65                  70                  75                  80
Ser Arg Asp Leu Val Val Ser Tyr Val Asn Thr Asn Met Gly Leu Lys
                85                  90                  95
Phe Arg Gln Leu Leu Trp Phe His Ile Ser Cys Leu Thr Phe Gly Arg
            100                 105                 110
Glu Thr Val Ile Glu Tyr Leu Val Ser Phe Gly Val Trp Ile Arg Thr
        115                 120                 125
Pro Pro Ala Tyr Arg Pro Pro Asn Ala Pro Ile Leu Ser Thr Leu Pro
    130                 135                 140
Glu Asn Thr Val Val Arg Arg Arg Gly Arg Ser Pro Arg Arg Arg Thr
145                 150                 155                 160
Pro Ser Pro Arg Arg Arg Arg Ser Gln Ser Pro Arg Arg Arg Arg Ser
                165                 170                 175
Gln Ser Pro Ala Ser Gln Cys
            180

<210> SEQ ID NO 19
<211> LENGTH: 183
<212> TYPE: PRT
<213> ORGANISM: hepatitis B virus

<400> SEQUENCE: 19

Met Asp Ile Asp Pro Tyr Lys Glu Phe Gly Ala Ser Val Glu Leu Leu
1               5                   10                  15
Ser Phe Leu Pro Ser Asp Phe Phe Pro Ser Val Arg Asp Leu Leu Asp
            20                  25                  30
Thr Ala Ser Ala Leu Tyr Arg Asp Ala Leu Glu Ser Pro Glu His Cys
        35                  40                  45
Thr Pro Asn His Thr Ala Leu Arg Gln Ala Ile Leu Cys Trp Gly Glu
    50                  55                  60
Leu Met Thr Leu Ala Ser Trp Val Gly Asn Asn Leu Glu Asp Pro Ala
65                  70                  75                  80
```

```
Ala Arg Asp Leu Val Val Asn Tyr Val Asn Thr His Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Pro Ala Ser Gln Cys
            180
```

<210> SEQ ID NO 20
<211> LENGTH: 183
<212> TYPE: PRT
<213> ORGANISM: hepatitis B virus

<400> SEQUENCE: 20

```
Met Asp Ile Asp Pro Tyr Lys Glu Phe Gly Ala Ser Ala Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Thr Pro Asn His Thr Ala Leu Arg Gln Ala Ile Leu Cys Trp Gly Glu
        50                  55                  60

Leu Met Thr Leu Ala Ser Trp Val Gly Asn Asn Leu Gln Asp Pro Ala
65                  70                  75                  80

Ala Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Gln Arg Gly Arg Ala Pro Arg Arg Arg Thr
145                 150                 155                 160

Pro Ser Pro Arg Arg Arg Ser Gln Ser Pro Arg Arg Arg Ser
                165                 170                 175

Gln Ser Pro Ala Ser Gln Cys
            180
```

<210> SEQ ID NO 21
<211> LENGTH: 195
<212> TYPE: PRT
<213> ORGANISM: hepatitis B virus

<400> SEQUENCE: 21

```
Met Asp Arg Thr Thr Leu Pro Tyr Gly Leu Phe Gly Leu Asp Ile Asp
1               5                   10                  15

Pro Tyr Lys Glu Phe Gly Ala Thr Val Glu Leu Leu Ser Phe Leu Pro
                20                  25                  30
```

```
Ser Asp Phe Phe Pro Ser Val Arg Asp Leu Leu Asp Thr Ala Ser Ala
        35                  40                  45

Leu Tyr Arg Glu Ser Leu Glu Ser Ser Asp His Cys Ser Pro His His
    50                  55                  60

Thr Ala Leu Arg Gln Ala Ile Leu Cys Trp Gly Glu Leu Met Thr Leu
65                  70                  75                  80

Ala Thr Trp Val Gly Asn Asn Leu Glu Asp Pro Ala Ser Arg Asp Leu
                85                  90                  95

Val Val Asn Tyr Val Asn Thr Asn Met Gly Leu Lys Ile Arg Gln Leu
                100                 105                 110

Leu Trp Phe His Ile Ser Cys Leu Thr Phe Gly Arg Glu Thr Val Leu
            115                 120                 125

Glu Tyr Leu Val Ser Phe Gly Val Trp Ile Arg Thr Pro Pro Ala Tyr
            130                 135                 140

Arg Pro Pro Asn Ala Pro Ile Leu Ser Thr Leu Pro Glu Thr Thr Val
145                 150                 155                 160

Val Arg Arg Arg Gly Arg Ser Pro Arg Arg Arg Thr Pro Ser Pro Arg
                165                 170                 175

Arg Arg Ser Gln Ser Pro Arg Arg Arg Ser Ala Ser Pro Ala
            180                 185                 190

Ser Gln Cys
        195

<210> SEQ ID NO 22
<211> LENGTH: 552
<212> TYPE: DNA
<213> ORGANISM: hepatitis B virus

<400> SEQUENCE: 22
atggacatcg acccctacaa agaattcggc gccagcgtgg aactgctgag cttcctgccc      60
agcgacttct cccctccat ccgggacctg ctggatacag ccagcgccct gtatagagag     120
gccctggaaa gccccgagca ctgcagccct catcacaccg ctctgagaca ggccatcctg     180
tgctggggcg agctgatgaa tctggccacc tgggtgggaa gcaacctgga agatcccgcc     240
agccgggaac tggtggtgtc ctacgtgaac gtgaacatgg gcctgaagat ccggcagctg     300
ctgtggttcc acatctcctg cctgaccttc ggcggaaaa ccgtgctgga atacctggtg     360
tccttcggcg tgtggatcag aacccccct gcctacagac ccccaacgc ccctatcctg     420 agcaccctgc ctgagacaac agtcgtgcgg cggagaggca aagcccag aagaagaacc     480 cccagcccca gacgcagaag aagccagtcc cctcggcgga aagatccca gagcagggaa     540 agccagtgct ag                                                        552

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
acaggtcggt ttccaggttg                                                 20

<210> SEQ ID NO 24
<211> LENGTH: 20
<212> TYPE: DNA
<213> ORGANISM: Artificial
```

```
<220> FEATURE:
<223> OTHER INFORMATION: primer

<400> SEQUENCE: 24
ggacatcaag gtggtgttca                                                  20

<210> SEQ ID NO 25
<211> LENGTH: 558
<212> TYPE: DNA
<213> ORGANISM: hepatitis B virus

<400> SEQUENCE: 25
atggacattg acccttataa agaatttgga gctactgtgg agttactctc gttttttgcct      60 tctgactttt ttccttccgt cagagatctc ctagacaccg cctcagctct gtatcgggaa     120
gccttagagt ctcctgagca ttgctcacct caccatactg cactcaggca agcaattctc     180
tgctgggggg aattgatgac tctagctacc tgggtgggta ataatttgga agatccagca     240
tccagggatc tagtagtcaa ttatgttaat actaacatgg gtttaaagat caggcaacta     300
ttgtggtttc atatatcttg ccttactttt ggaagagaga ctgtacttga atatttggtc     360
tctttcggag tgtggattcg cactcctcca gcctatagac caccaaatgc ccctatctta     420
tcaacacttc cggaaactac tgttgttaga cgacgggacc gaggcaggtc ccctagaaga     480
agaactccct cgcctcgcag acgcagatct caatcgccgc gtcgcagaag atctcaatct     540
cgggaatctc aatgttag                                                  558

<210> SEQ ID NO 26
<211> LENGTH: 552
<212> TYPE: DNA
<213> ORGANISM: hepatitis B virus

<400> SEQUENCE: 26
atggacattg atccatataa agaatttgga gctactgtgg agttactctc gttttttgcct     60 tctgacttct ttccttcagt acgagatctt ctagataccg cctccgctct atatcgggaa     120
gccttagagt ctcctgagca ttgttcacct caccatactg cactcaggca agccattctt     180
tgctgggggg aactaatgac tctggccacc tgggtgggtg gtaatttgga agatccaata     240
tccagggacc tggtagtcag ttatgttaac actaatatgg gcctaaagtt caggcaacta     300
ttgtggtttc acatttcttg tctcactttt ggaagagaaa cggtcataga gtatttggtg     360
tctttcggag tgtggattcg cactcctcca gcttatagac caccaaatgc ccctatctta     420
tcaacacttc cggagactac tgttgttaga cgacgaggcg gtcccctag aagaagaact     480 ccctcgcctc gcagacgaag gtctcaatcg ccgcgtcgca agatctcaa atctcgggaa     540 tctcaatgtt ag                                                        552

<210> SEQ ID NO 27
<211> LENGTH: 552
<212> TYPE: DNA
<213> ORGANISM: hepatitis B virus

<400> SEQUENCE: 27
atggacattg acccttataa agaatttgga gctactgtgg agttactctc gttttttgcct     60 tctgacttct ttccttcagt aagagatctt ctagataccg cctcagctct gtatcgggat     120
gccttagaat ctcctgaaca ttgttcaccg caccacactg cactcaggca agccattctt     180
tgctgggggg aactaatgac tctagctacc tgggtgggtg taaatttgga agatccagca     240
```

```
tccagggacc tagtagtcag ttatgtcaat actaatatgg gcctaaagtt caggcaatta    300
ttgtggtttc acatttcttg tctcactttt ggaagagaaa ccgtcataga gtatttggtg    360
tcttttggag tgtggattcg cactcctcca gcttatagac caccaaatgc ccctatctta    420
tcaacacttc cggagaatac tgttgttaga cgaagaggga ggtcccctag aagaagaact    480
ccctcgcctc gcagacgaag atctcaatcg ccgcgtcgca gaagatctca atctccagct    540
tcccaatgtt ag                                                        552

<210> SEQ ID NO 28
<211> LENGTH: 552
<212> TYPE: DNA
<213> ORGANISM: hepatitis B virus

<400> SEQUENCE: 28
atggacattg acccttataa agaatttgga gcttctgtgg aattactctc ttttttgcct     60
tctgatttct tcccgtcagt tcgggaccta ctcgacaccg cttcagccct ctaccgggat    120
gctttagaat caccagaaca ttgcacacct aaccataccg ctctcaggca agctatattg    180
tgctggggtg agttaatgac tttggcttcc tgggtgggca ataatttgga agatcctgct    240
gctagggacc tagtggttaa ctatgtcaat actcacatgg gcctaaaaat tagacaatta    300
ctgtggtttc acatttcctg ccttactttt ggaagagaaa cagttcttga gtatttggtg    360
tcttttggag tgtggattcg cactcctcct gcttatagac caccaaatgc ccctatctta    420
tccacacttc cggaaactac tgttgttaga cgacgaggca ggtcccctcg aagaagaact    480
ccctcgcctc gcagacgaag gtctcaatcg ccgcgtcgca gaagatctca atctccagct    540
tcccaatgtt ag                                                        552

<210> SEQ ID NO 29
<211> LENGTH: 15
<212> TYPE: PRT
<213> ORGANISM: hepatitis B virus

<400> SEQUENCE: 29

Pro Ala Tyr Arg Pro Pro Asn Ala Pro Ile Leu Ser Thr Leu Pro
1               5                   10                  15

<210> SEQ ID NO 30
<211> LENGTH: 12
<212> TYPE: PRT
<213> ORGANISM: Artificial
<220> FEATURE:
<223> OTHER INFORMATION: synthetic

<400> SEQUENCE: 30

Gly Val Ala Met Pro Gly Ala Glu Asp Asp Val Val
1               5                   10
```